(12) United States Patent
Gould et al.

(10) Patent No.: US 12,379,780 B2
(45) Date of Patent: Aug. 5, 2025

(54) MANUFACTURING PROCESSES FOR BIOPOTENTIAL-BASED WRIST-WEARABLE DEVICES AND RESULTING MANUFACTURED BIOPOTENTIAL-BASED WRIST-WEARABLE DEVICES

(71) Applicant: Meta Platforms Technologies, LLC, Menlo Park, CA (US)

(72) Inventors: Kyra Gould, Seattle, WA (US); Nicole Cullen, Redmond, WA (US); Pinghung Wei, Kirkland, WA (US); Keen Butcher, Redmond, WA (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 0 days.

(21) Appl. No.: 18/587,759

(22) Filed: Feb. 26, 2024

(65) Prior Publication Data

US 2024/0361838 A1 Oct. 31, 2024

Related U.S. Application Data

(60) Provisional application No. 63/498,797, filed on Apr. 27, 2023.

(51) Int. Cl.
*G06F 3/01* (2006.01)
(52) U.S. Cl.
CPC .................... *G06F 3/015* (2013.01)
(58) Field of Classification Search
CPC ........ G06F 3/015; G16H 40/63; G16H 40/67; A61B 5/0022; A61B 5/02438;
(Continued)

(56) References Cited

U.S. PATENT DOCUMENTS 4,103,808 A * 8/1978 Hallman .............. A44C 5/0053
368/286
11,758,991 B1 * 9/2023 Hegde ..................... D02G 3/32
368/282

(Continued)

FOREIGN PATENT DOCUMENTS

CN 113647964 A 11/2021

OTHER PUBLICATIONS

European Search Report for European Patent Application No. 24167542.0, dated Jul. 15, 2024, 6 pages.

*Primary Examiner* — Christopher E Leiby
(74) *Attorney, Agent, or Firm* — Morgan, Lewis & Bockius LLP

(57) ABSTRACT

A wrist-wearable device is described herein. The wrist wearable device includes a first skin-contact portion. The first skin contact portion (i) is coupled with a first set of biopotential-signal sensors for detecting first biopotential signals that are provided to a first flexible printed circuit board, and (ii) is coupled with an elastic material that extends beyond an end of the first skin-contact portion. The wrist wearable device includes a second skin-contact portion that is separated from the first skin-contact portion by a capsule structure. The second skin-contact portion is (ii) coupled with a second set of biopotential-signal sensors for detecting biopotential signals that are provided to a second flexible printed circuit board, and (ii) is coupled with a receiving loop for receiving the elastic material to affix the band to a body part of a wearer of the wrist-wearable device.

20 Claims, 13 Drawing Sheets

(58) Field of Classification Search
CPC ..... A61B 5/14551; A61B 5/277; A61B 5/296; A61B 5/7455; A61B 5/6803; A61B 5/256; A61B 5/6824; A61B 5/6898; A61B 5/681; A61B 2562/0219; A61B 2562/043; A61B 2562/046; A61B 2562/125; A61B 2562/164; A61B 2562/166

See application file for complete search history.

(56) References Cited

U.S. PATENT DOCUMENTS

| | | | | |
|---|---|---|---|---|
| 2015/0320588 | A1* | 11/2015 | Connor | F24F 11/0001 607/104 |
| 2019/0254390 | A1* | 8/2019 | Herz | A44C 5/0007 |
| 2021/0298395 | A1* | 9/2021 | Halpern | A41D 20/00 |
| 2021/0378571 | A1* | 12/2021 | King | A61B 5/332 |

* cited by examiner

MANUFACTURING PROCESSES FOR BIOPOTENTIAL-BASED WRIST-WEARABLE DEVICES AND RESULTING MANUFACTURED BIOPOTENTIAL -BASED WRIST-WEARABLE DEVICES

RELATED APPLICATIONS

This claims benefit of, and the priority to, U.S. Provisional Application Ser. No. 63/498,797, entitled "Manufacturing Processes for Biopotential-Based Wrist-Wearable Devices and Resulting Manufactured Biopotential Based Wrist-Wearable Devices" filed Apr. 27, 2023, the disclosure of which is incorporated in its entirety by this reference.

TECHNICAL FIELD

This relates generally to lightweight wrist-wearable devices that include a high density of biopotential sensors (e.g., biopotential sensors located on both bands of the wrist-wearable device) configured to detect one or more biopotential signals of a wearer. The wrist-wearable device also makes use of elastic materials to allow for easy donning and doffing while also being configured to accommodate many varying wrist sizes. Manufacturing processes are also described herein as the manufacturing process is an important aspect in creating such a lightweight wrist-wearable device.

BACKGROUND

Wrist-wearable devices used in conjunction with artificial realities tend to have issues with either weight or low fidelity. For example, wrist-wearable devices that are lightweight do not have enough sensors to produce the high-fidelity data that is required to interact with an artificial reality (e.g., a low density of sensors located on only one portion of a wrist-wearable device). In another example, wrist-wearable devices that do have enough sensors to produce high-fidelity data are heavy, which reduces the time in which a wearer can comfortably wear the wrist-wearable device. Thus, traditional wrist-wearable devices suffer a dichotomy between choosing to make the wrist wearable device lightweight or make the wrist-wearable device produce high fidelity data.

As such, there is a need to address one or more of the above-identified challenges, including making a wrist-wearable device that is both lightweight and provides high-fidelity data to be used in conjunction with an artificial reality. A brief summary of solutions to the issues noted above are described below.

SUMMARY

The wrist-wearable devices and their accompanying manufacturing process described herein resolve the dichotomy between weight and fidelity of data described above. The wrist-wearable device herein uses an extensive number of biopotential sensors located on both bands of the wrist-wearable device, thereby utilizing substantially all of the wrist-facing real estate. Additionally, the wrist-wearable device is slim in nature and is as only as wide as required to encapsulate the embedded flexible printed circuit board and accompanying biopotential sensors. In addition, the wrist-wearable device also makes use of simple attachment components, such as, Velcro and simply looping an elastic structure extending from a first side through a receiving loop attached at an opposite second side. These manufacturing techniques and design choices, in part, allow for the wrist-wearable device to be both lightweight and produce high fidelity biopotential data.

One example of an wrist-wearable device is described herein. This example wrist-wearable device includes a first skin-contact portion of a band of the wrist-wearable device (e.g., first skin contact portion 262A of wrist-wearable device 272 in FIGS. 2A-2D) that: (i) includes a first flexible printed circuit board (e.g., flexible printed circuit board 210A shown in FIG. 2A), (ii) is coupled with a first set of biopotential-signal sensors for detecting first biopotential signals that are provided to the first flexible printed circuit board (e.g., biopotential sensors 204A-204J depicted in FIG. 2A), and (iii) is coupled with an elastic material that extends beyond an end of the first skin-contact portion of the band (e.g., elastic band 224A extends beyond the textile 218, as shown in FIGS. 2B and 2D). The wrist-wearable device also comprises a second skin-contact portion of the band of the wrist-wearable device (e.g., second skin contact portion 262B of wrist-wearable device 272 in FIGS. 2A-2D) that is separated from the first skin-contact portion of the band by a capsule structure (e.g., capsule 270 as shown in FIG. 2D), the second skin-contact portion: (i) includes a second flexible printed circuit board (e.g., flexible printed circuit board 210B shown in FIG. 2A), (ii) coupled with a second set of biopotential-signal sensors for detecting biopotential signals that are provided to the second flexible printed circuit board (e.g., biopotential sensors 204K-204P depicted in FIG. 2A), and (iii) is coupled with a receiving loop (e.g., receiving loop 232 shown in FIGS. 2B-2D) for receiving the elastic material (e.g., elastic band 224A) to affix the band to a body part (e.g., wrist 106 of user 102 as shown in FIG. 1) of a wearer of the wrist-wearable device. In some embodiments, the first skin-contact portion and the second skin-contact portion are made of a same material that is distinct from the elastic material (e.g., wrist-facing textile 238 is different from the elastic bands 224A and 224B), such that when the wrist-wearable device is worn on the wrist of a user the elastic material is configured to stretch to affix the band to the wrist of the user through the receiving loop and the first and second skin-contact portions are not configured to stretch.

The features and advantages described in the specification are not necessarily all inclusive and, in particular, certain additional features and advantages will be apparent to one of ordinary skill in the art in view of the drawings, specification, and claims. Moreover, it should be noted that the language used in the specification has been principally selected for readability and instructional purposes.

Having summarized the above example aspects, a brief description of the drawings will now be presented.

BRIEF DESCRIPTION OF THE DRAWINGS

For a better understanding of the various described embodiments, reference should be made to the Detailed Description below, in conjunction with the following drawings in which like reference numerals refer to corresponding parts throughout the figures.

Figure 1:
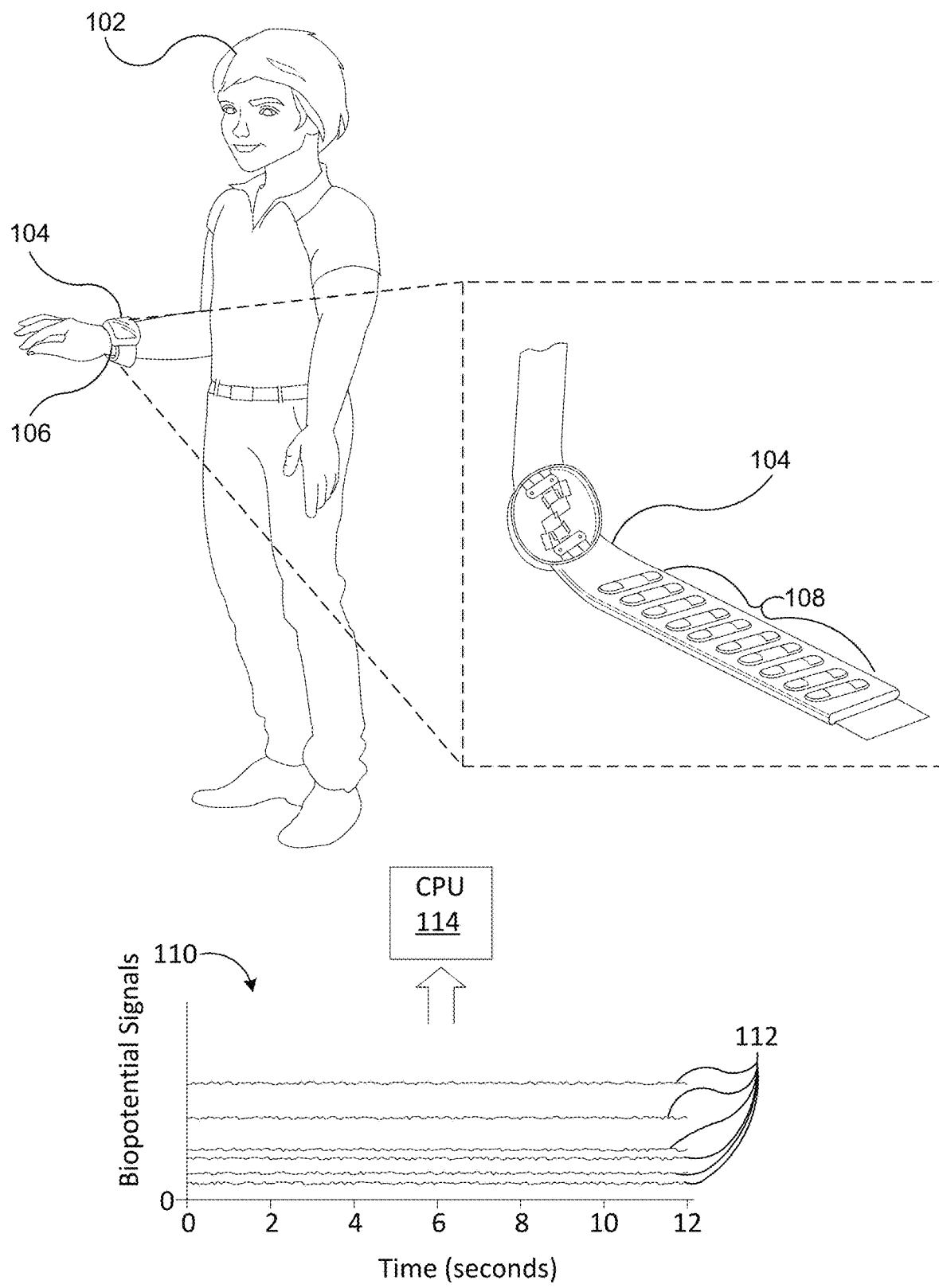
FIG. 1 illustrates a user wearing a wrist-wearable device that is configured to detect one or more biopotential signals of a wearer of the wrist-wearable device, in accordance with some embodiments.

In accordance with common practice, the various features illustrated in the drawings may not be drawn to scale. Accordingly, the dimensions of the various features may be arbitrarily expanded or reduced for clarity. In addition, some of the drawings may not depict all of the components of a given system, method, or device. Finally, like reference numerals may be used to denote like features throughout the specification and figures.

DETAILED DESCRIPTION

Numerous details are described herein to provide a thorough understanding of the example embodiments illustrated in the accompanying drawings. However, some embodiments may be practiced without many of the specific details, and the scope of the claims is only limited by those features and aspects specifically recited in the claims. Furthermore, well-known processes, components, and materials have not necessarily been described in exhaustive detail so as to avoid obscuring pertinent aspects of the embodiments described herein.

Embodiments of this disclosure can include or be implemented in conjunction with various types or embodiments of artificial-reality systems. Artificial-reality, as described herein, is any superimposed functionality and or sensory-detectable presentation provided by an artificial-reality system within a user's physical surroundings. Such artificial-realities (AR) can include and/or represent virtual reality (VR), augmented reality, mixed artificial-reality (MAR), or some combination and/or variation one of these. For example, a user can perform a swiping in-air hand gesture to cause a song to be skipped by a song-providing API providing playback at, for example, a home speaker. In some embodiments of an AR system, ambient light (e.g., a live feed of the surrounding environment that a user would normally see) can be passed through a display element of a respective head-wearable device presenting aspects of the AR system. In some embodiments, ambient light can be passed through respective aspect of the AR system. For example, a visual user interface element (e.g., a notification user interface element) can be presented at the head-wearable device, and an amount of ambient light (e.g., 15-50% of the ambient light) can be passed through the user interface element, such that the user can distinguish at least a portion of the physical environment over which the user interface element is being displayed.

Artificial-reality content can include completely generated content or generated content combined with captured (e.g., real-world) content. The artificial-reality content can include video, audio, haptic events, or some combination thereof, any of which can be presented in a single channel or in multiple channels (such as stereo video that produces a three-dimensional effect to a viewer). Additionally, in some embodiments, artificial reality can also be associated with applications, products, accessories, services, or some combination thereof, which are used, for example, to create content in an artificial reality and/or are otherwise used in (e.g., to perform activities in) an artificial reality.

To interact with artificial realities input devices are needed, especially high accuracy lightweight ones. To that end, a wrist-wearable device that is both lightweight and has a high density of biopotential sensors is described herein. Due to its high-density nature and low weight, the manufacturing process of this wrist wearable device will also be discussed in detail herein. Having more biopotential sensors allows for less noise in the biopotential signals and also allows for a greater range of inputs to be determined.

FIG. 1 illustrates a user wearing a wrist-wearable device that is configured to detect one or more biopotential signals of a wearer of the wrist-wearable device, in accordance with some embodiments. FIG. 1 shows a user 102 wearing a wrist-wearable device 104 about their wrist 106. As we will be discussed in further detail in relation to subsequent Figures, the wrist-wearable device 104 is configured with a plurality of biopotential signal sensors 108. This plurality of biopotential sensors 108 is configured to detect one or more biopotential signals of the user 102. In some embodiments, these detected signals can be used to provide inputs to an artificial reality headset (described in reference to FIGS. 5A-5B and 6A-6B). Chart 110, shown beneath the depiction of the user 102, illustrates the recorded biopotential signals 112 detected by the plurality of biopotential signal sensors 108 of the wrist-wearable device 104. In some embodiments, the recorded biopotential signals 112 are sent to a processor 114 for processing (e.g., signal filtering, determining gestures being performed, etc.).

Figure 2A:
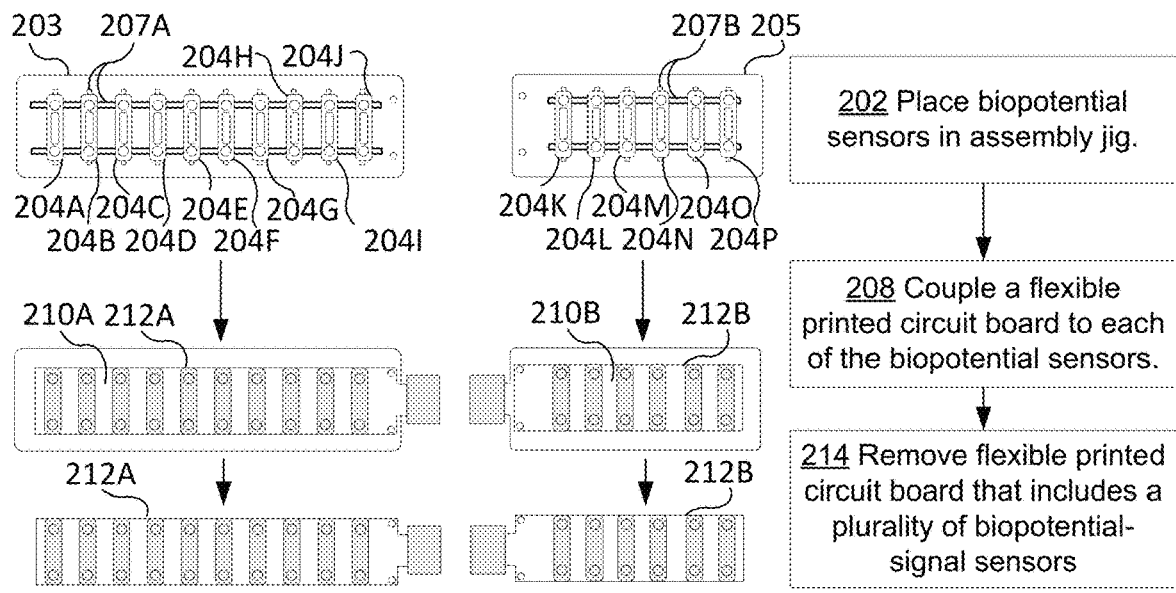
FIGS. 2A-2D illustrate an assembly process for producing a lightweight wrist-wearable device (e.g., wrist wearable device 104 shown in FIG. 1) that includes a high density of biopotential sensors that are configured to be in contact with a wrist of a user, in accordance with some embodiments.

FIGS. 2A-2D illustrate an assembly process for producing a lightweight wrist-wearable device (e.g., wrist wearable device 104 shown in FIG. 1) that includes a high density of biopotential sensors that are configured to be in contact with a wrist of a user, in accordance with some embodiments. FIG. 2A shows a sequence for producing a biopotential sensor sub-assembly that is used in the wrist-wearable device described in reference to FIGS. 2A-2D. Two biopotential sensor sub-assemblies are produced, one for a first skin contact portion and another for a second skin contact portion (e.g., similar to two portions of a watch band).

In manufacturing step 202 of the production sequence 200, a first assembly jig 203 and a second assembly jig 205 are shown, and each of the first assembly jig 203 and the assembly jig 205 include guiding indentations 207A and 207B for aligning a plurality of biopotential sensors 204A-204P. Manufacturing step 202 also shows a plurality of biopotential sensors 204A-204J placed into the guiding indentations 207A, and biopotential sensors 204K-204P placed into guiding indentations 207B. In some embodiments, the assembly jigs 203 and 205 are rigid structure (e.g., produced from a metal/alloy) that is not easily flexed to maintain consistency between production runs.

In manufacturing step 208 flexible printed circuit boards 210A and 210B are coupled to biopotential sensors 204A-204J (obscured and not labeled) and biopotential sensors 204K-204P (obscured and not labeled), respectively, to produce a first biopotential assembly 212A and second biopotential assembly 212B. In some embodiments, the biopotential sensors are soldered to the circuit boards or are press fitted into place.

In manufacturing step 214 of the production sequence 200 shows that the first biopotential assembly 212A and second biopotential assembly 212B are removed from first assembly jig 203 and the assembly jig 205, respectively. These first biopotential assembly 212A and second biopotential assembly 212B are then set aside for later assembly (see, FIGS. 2C-2D).

Figure 2B:
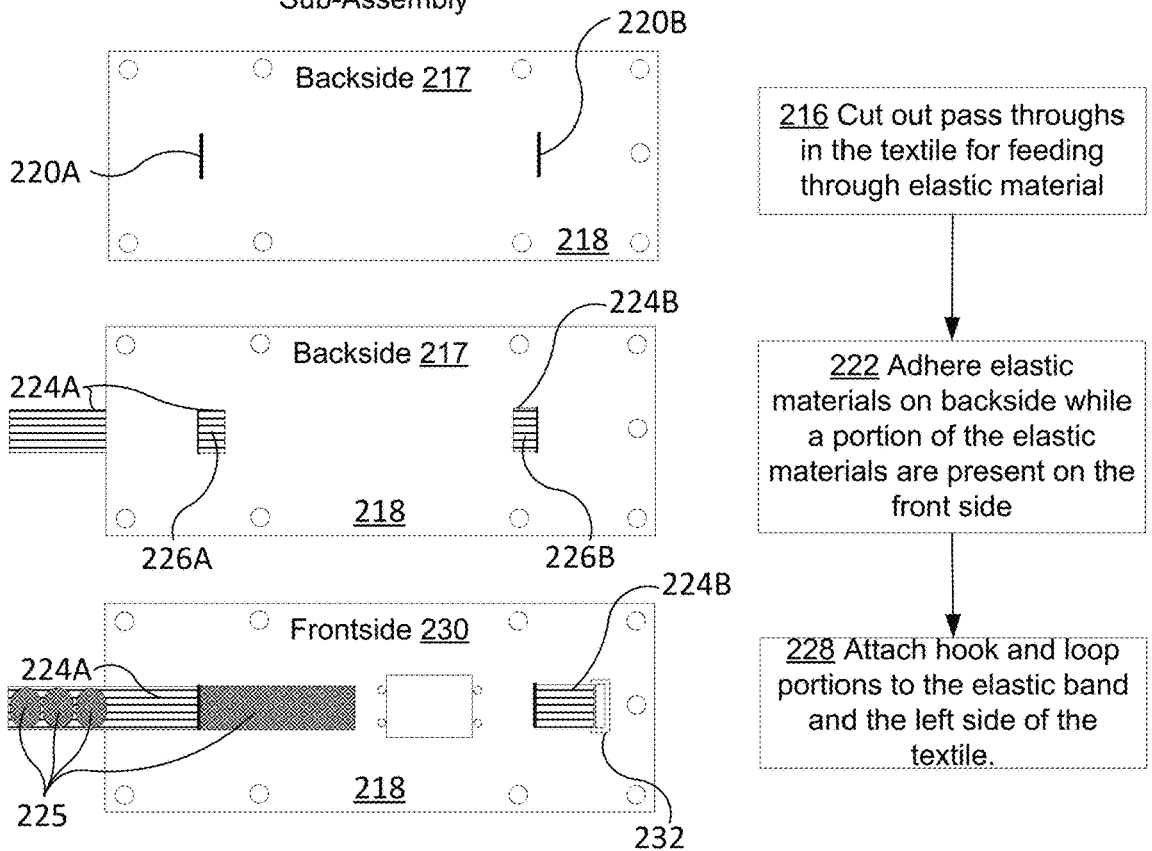

FIG. 2B shows a sequence for producing an outside facing band sub-assembly that is used in the wrist-wearable device described in reference to FIGS. 2A-2D. Manufacturing step 216 shows a backside 217 of a textile 218 that has two cutouts 220A and 220B that are configured to pass elastic bands through them.

Manufacturing step 222 shows a backside 217 of the textile 218 that now includes elastic bands 224A and 224B that are attached at opposite ends of the textile 218. The elastic bands 224A and 224B have respective portions 226A and 226B that are adhered to the backside of the textile 218. In some embodiments, the respective portions 226A and 226B are adhered using an adhesive. In some embodiments, the elastic bands 224A and 224B are further adhered by being sewn onto the textile 218.

Manufacturing step 228 shows a frontside 230 of the textile 218, which shows that the elastic band 224A includes hook and loop portions 225 (e.g., Velcro), and elastic band 224B includes a receiving loop 232 that is configured to receive the elastic band 224A. As will be described late, the receiving loop 232 is configured to be used in conjunction with the elastic band 224A to secure the wrist-wearable device to the user' wrist. Frontside 230 also shows a corresponding hook and loop portion 234 configured to adhere to the hook and loop portion 225 after it has passed through the loop 232. After this is completed an non-wrist-facing sub-assembly 236 is produced, and this non-wrist-facing sub-assembly 236 is then set aside for later use during the production process. In some embodiments, elastic band 224B extends ¼ inch to 1 inch on the frontside 230. In some embodiments, the elastic band 224A extends 2-6 inches on the frontside. In some embodiments, the end of the elastic band 224A is folded over itself (e.g., fold over at a minimum of ⅖ inches) and sewn and/or adhered into place. In some embodiments, the hook portion and the loop portion of the hook and loop 225 (e.g., Velcro) are separated by at least two inches from each other (e.g., 3.5 inches).

Figure 2C:
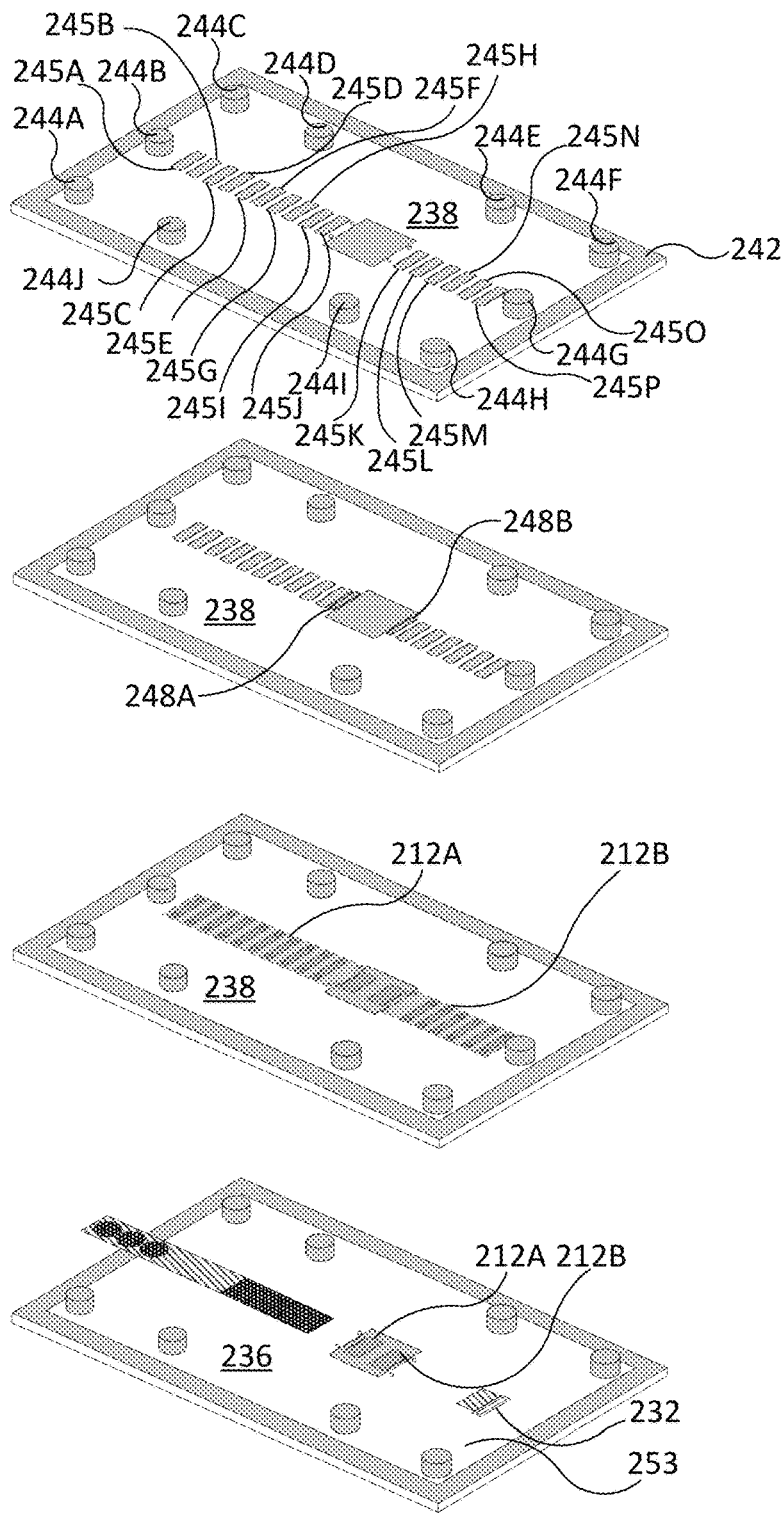

FIG. 2C shows a sequence of combining wrist-facing textile 238 to the sub-assemblies described in reference to both FIGS. 2A-2B. Manufacturing step 240 shows wrist-facing textile 238 being placed on jig 242, where jig 242 includes posts 244A-244J for aligning the wrist-facing textile 238 that includes corresponding cutouts. In some embodiments, more or less posts are used for aligning the wrist-facing textile (e.g., as few as two posts). Wrist-facing textile 238 is also configured to be the textile that is contact with a wrist of the user and includes a first set of cutouts 245A-245J and a second set of cutouts 245K-245P that correspond to biopotential sensors 204A-204J and biopotential sensors 204K-204P, respectively.

Manufacturing step 246 shows that a reinforcement plates 248A and 248B are bonded to the wrist-facing textile 238. In some embodiments, these reinforcement plates 248A and 248B are configured to take a tensioning load instead of the first biopotential assembly 212A (shown in FIG. 2A) and second biopotential assembly 212B (shown in FIG. 2A) taking the tensioning load. In other words, these reinforcement plates 248A and 248B ensure that the textile does not become detached from a capsule (described in reference to FIG. 2D), as a result of the weaker nature of a flexible printed circuit board material. In some embodiments, the adhesive is pre-tacked prior to applying the reinforcement plates 248A and 248B. In some embodiments, the reinforcement plates 248A and 248B are made of alloys/metals, such as stainless steel. In some embodiments, the adhesive is Bemis 3412 or MT413 and are fully cured using one or more of pre-tacking and a heat press. In some embodiments, isopropyl alcohol is applied prior to applying an adhesive.

Manufacturing step 250 shows that first biopotential assembly 212A and second biopotential assembly 212B are coupled with the wrist-facing textile 238, such that the first set of cutouts 245A-245J (obscured, labeled in manufacturing step 240) and a second set of cutouts 245K-245P (obscured, labeled in manufacturing step 240) are aligned with corresponding biopotential sensors 204A-204J (obscured, labeled in FIG. 2A) and biopotential sensors 204K-204P (obscured, labeled in FIG. 2A), respectively. In some embodiments, the first set of cutouts 245A-245J (obscured, labeled in manufacturing step 240) and a second set of cutouts 245K-245P (obscured, labeled in manufacturing step 240) are produced using a laser cutter. In some embodiments, the electrodes are oversized for the hole ensuring that exposed edges of the wrist-facing textile 238 are covered by a biopotential sensor. In some embodiments, a respective additional skin contact portion of the biopotential sensor is press fit onto the biopotential sensors 204A-204P (obscured, labeled in FIG. 2A) to further (i) couple the wrist-facing textile 238 to the first biopotential assembly 212A and second biopotential assembly 212B, and/or (ii) remove any exposed edges of the textile from being exposed (e.g., to avoid fraying. In some embodiments, the first biopotential assembly 212A and second biopotential assembly 212B are further coupled with the wrist-facing textile 238 using an adhesive.

Manufacturing step 252 shows that an non-wrist-facing sub-assembly 236, described in reference to FIG. 2B, is adhered to wrist-facing textile 238 (obscured), the first biopotential assembly 212A, and second biopotential assembly 212B to produce a non-cut wristband assembly 253. In other words, the first biopotential assembly 212A and second biopotential assembly 212B are sandwiched between the wrist-facing textile 238 and non-wrist-facing sub-assembly 236. In some embodiments, an adhesive is applied to one or more of non-wrist-facing sub-assembly 236, wrist-facing textile 238 (obscured), first biopotential assembly 212A and/or second biopotential assembly 212B to bond them together. In some embodiments, the adhesive used requires heat to finish the bonding process. For example, adhesives such as HAF 3412 can be used for the adhesive, which requires a pre-tacking at 100-150 degrees Fahrenheit for 1-3 seconds. After pre-tacking is complete, the entire non-cut assembly 253 can be placed into a heat press for 10-60 seconds at a temperature of 100-200 degrees Fahrenheit. In some embodiments, pre-tacking starts at the most stressed locations first, such as the reinforcement plate(s) 248A and 248B (obscured) and the receiving loop 232 locations.

Figure 2D:
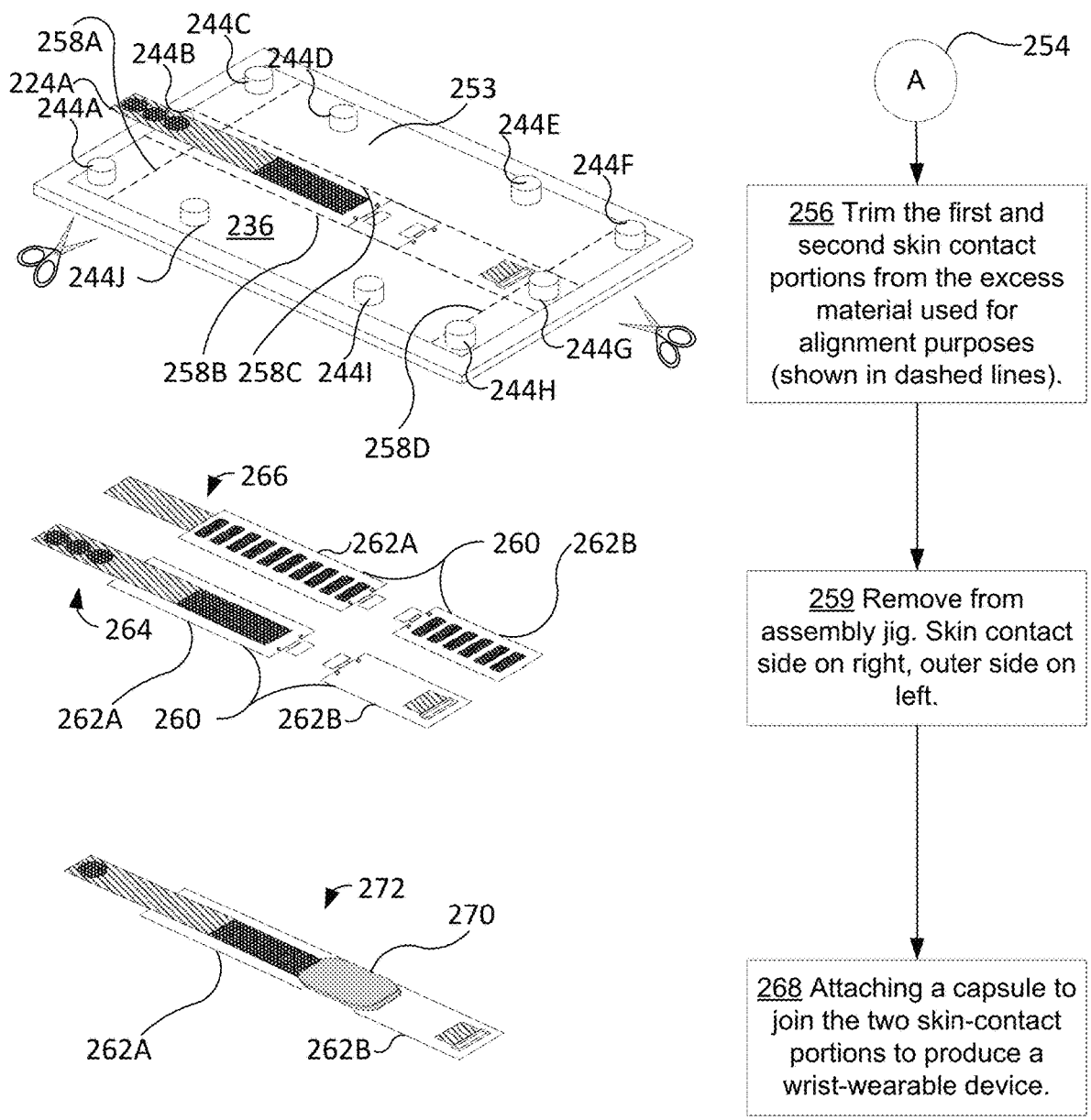

The manufacturing process is continued in FIG. 2D, as illustrated by "A" 254 shown in both FIGS. 2C and 2D. FIG. 2D shows in manufacturing step 256 that non-cut assembly 253 is cut along the dashed lines 258A-258D. While manufacturing step 256 appears to show that elastic band 224A is trimmed, it is not, and only the wrist-facing textile 238 (obscured) and the textile portion of non-wrist-facing sub-assembly 236 are trimmed. In some embodiments, cutting guides can be placed on the posts 244A-244J to ensure that trimming is consistent and that the underlying first biopotential assembly 212A and/or second biopotential assembly 212B are not accidentally scored. In some embodiments, this trimming process can be done either automatically or by manually. In some embodiments, the trimming process described above can occur via the use of a laser cutter.

Manufacturing process 259 shows a the non-wrist-facing view 264 and the wrist-facing view 266 of non-coupled band assembly 260, that includes a first skin contact portion 262A and a second skin contact portion 262B. being removed from the jig assembly. Two non-coupled band assemblies are shown for explanation/illustration purposes to show the non-wrist-facing view 264 and the wrist-facing view 266 of the non-coupled band assemblies 260, despite only one being produced during this example manufacturing process.

Manufacturing process 268 shows that a capsule 270 being configured to join the first skin contact portion 262A and a second skin contact portion 262B together to produce a wrist-wearable device 272. In some embodiments, the capsule includes one or more processors, one or more communications components, and one or more biopotential sensors. In some embodiments, the capsule includes components that are electrically coupled to both biopotential sensors 204A-204J and biopotential sensors 204K-204P. In some embodiments, the capsule 270 is secured by one or more of: adhesive, screws into the reinforcement plates 248A and 248B, and press fittings.

While some of the above examples show the process taking place in a jig, it is conceivable that some if not all steps could occur without the use of a jig assembly and/or without any alignment techniques. For example, other alignment techniques can be used, such as sewing portions together, pinning portions down using clamps, using pins, etc., While many adhesive steps are discussed above, in some embodiments, these adhesives require the use of heat to properly bond. As such the jigs described above can be configured to be placed into a heat press machines without needing to remove anything from the jigs (e.g., removing an non-wrist-facing sub-assembly 236, wrist-facing textile 238, first biopotential assembly 212A, or second biopotential assembly 212B). Such an approach ensures that proper alignment is maintained during the manufacturing process.

While wrist-wearable devices are described, the processes described above can be used to make any form of wearable device, such as a headband, anklet, or any other location on the body where biopotential signals can be recorded.

Figure 3:
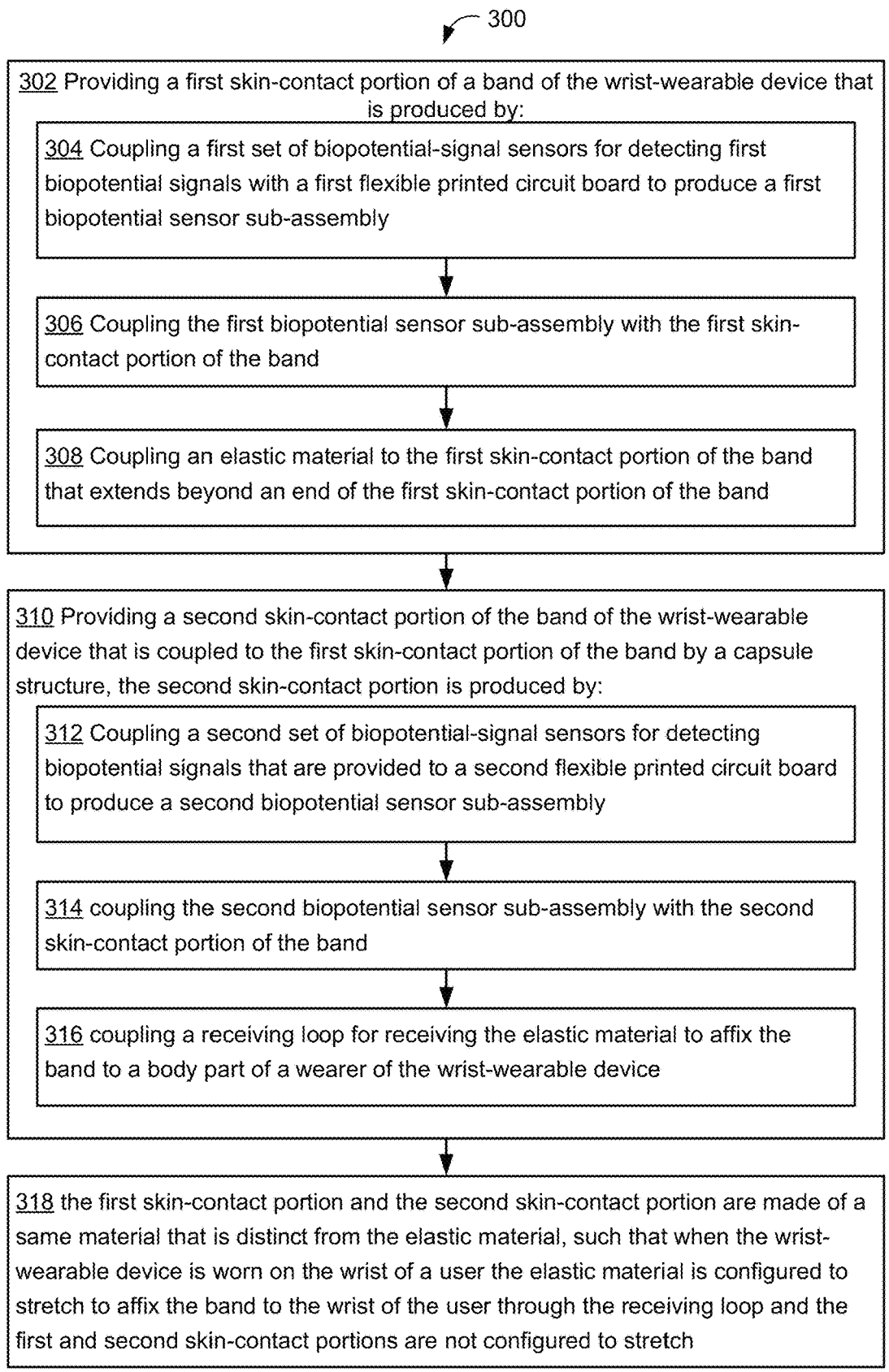
FIG. 3 shows an example method flow chart for manufacturing a lightweight wrist-wearable device that includes a plurality of biopotential sensors, in accordance with some embodiments.

FIG. 3 shows an example method flow chart 300 for manufacturing a lightweight wrist-wearable device that includes a plurality of biopotential sensors, in accordance with some embodiments. While FIGS. 2A-2D illustrate a method of manufacturing, the flow chart 300 is meant to augment what is described in FIGS. 2A-2D and is not intended to limit what is disclosed in FIGS. 2A-2D. In addition, the order and operations described in method flow chart 300 can be applied to the method of manufacturing described in FIGS. 2A-2D, and vice versa.

(A1) In accordance with some embodiments a method of manufacturing 300 a wrist-wearable device comprises, providing (302) a first skin-contact portion of a band of the wrist-wearable device (e.g., first skin contact portion 262A of wrist-wearable device 272 in FIGS. 2A-2D) that is produced by: (i) coupling (304) a first set of biopotential-signal sensors for detecting first biopotential signals with a first flexible printed circuit board (e.g., biopotential sensors 204A-204J depicted in FIG. 2A) to produce a first biopotential sensor sub-assembly; (ii) coupling (306) the first biopotential sensor sub-assembly with the first skin-contact portion of the band; and (iii) coupling (308) an elastic material to the first skin-contact portion of the band that extends beyond an end of the first skin-contact portion of the band (e.g., elastic band 224A extends beyond the textile 218, as shown in FIGS. 2B and 2D). The method of manufacturing also includes, providing (310) a second skin-contact portion of the band of the wrist-wearable device (e.g., second skin contact portion 262B of wrist-wearable device 272 in FIGS. 2A-2D) that is coupled to the first skin-contact portion of the band by a capsule structure (e.g., capsule 270 as shown in FIG. 2D), the second skin-contact portion is produced by: (i) coupling (312) a second set of biopotential-signal sensors (e.g., biopotential sensors 204K-204P depicted in FIG. 2A) for detecting biopotential signals that are provided to a second flexible printed circuit board (e.g., flexible printed circuit board 210B shown in FIG. 2A) to produce a second biopotential sensor sub-assembly; (ii) coupling (314) the second biopotential sensor sub-assembly with the second skin-contact portion of the band; and (iii) coupling (316) a receiving loop (e.g., receiving loop 232 shown in FIGS. 2B-2D) for receiving the elastic material (e.g., elastic band 224A) to affix the band to a body part (e.g., wrist 106 of user 102 as shown in FIG. 1) of a wearer of the wrist-wearable device. In some embodiments, the first skin-contact portion and the second skin-contact portion are made of a same material that is distinct from the elastic material (e.g., wrist-facing textile 238 is different from the elastic bands 224A and 224B), such that when the wrist-wearable device is worn on a wrist of a user the elastic material is configured to stretch to affix the band to the wrist of the user through the receiving loop and the first and second skin-contact portions are not configured to stretch (318).

(A2) In some embodiments of A1, the first skin-contact portion of the band and the second skin-contact portion are part of the same continuous textile that was configured to be placed in a jig-alignment assembly. In some embodiments, the method of manufacturing further includes, trimming the first skin-contact portion of the band and the second skin-contact portion to produce a first trimmed-skin-contact portion of the band and a second trimmed-skin-contact portion, wherein the first trimmed-skin-contact portion of the band and the second trimmed-skin-contact portion are configured to be separately coupled to the capsule structure.

(A3) In some embodiments of A2, the method of manufacturing the wrist-wearable device further includes, coupling the first trimmed-skin-contact portion of the band and the second trimmed-skin-contact portion to opposite sides of the capsule structure to produce the wrist-wearable device.

(B1) In accordance with some embodiments, a wrist-wearable device, comprises a first skin-contact portion of a band of the wrist-wearable device (e.g., first skin contact portion 262A of wrist-wearable device 272 in FIGS. 2A-2D) that: (i) includes a first flexible printed circuit board (e.g., flexible printed circuit board 210A shown in FIG. 2A), (ii) is coupled with a first set of biopotential-signal sensors for detecting first biopotential signals that are provided to the first flexible printed circuit board (e.g., biopotential sensors 204A-204J depicted in FIG. 2A), and (iii) is coupled with an elastic material that extends beyond an end of the first skin-contact portion of the band (e.g., elastic band 224A extends beyond the textile 218, as shown in FIGS. 2B and 2D). The wrist-wearable device also comprises a second skin-contact portion of the band of the wrist-wearable device (e.g., second skin contact portion 262B of wrist-wearable device 272 in FIGS. 2A-2D) that is separated from the first skin-contact portion of the band by a capsule structure (e.g., capsule 270 as shown in FIG. 2D), the second skin-contact portion: (i) includes a second flexible printed circuit board (e.g., flexible printed circuit board 210B shown in FIG. 2A), (ii) coupled with a second set of biopotential-signal sensors for detecting biopotential signals that are provided to the second flexible printed circuit board (e.g., biopotential sensors 204K-204P depicted in FIG. 2A), and (iii) is coupled with a receiving loop (e.g., receiving loop 232 shown in FIGS. 2B-2D) for receiving the elastic material (e.g., elastic band 224A) to affix the band to a body part (e.g., wrist 106 of user 102 as shown in FIG. 1) of a wearer of the wrist-wearable device. In some embodiments, the first skin-contact portion and the second skin-contact portion are made of a same material that is distinct from the elastic material (e.g., wrist-facing textile 238 is different from the elastic bands 224A and 224B), such that when the wrist-wearable device is worn on the wrist of a user the elastic material is configured to stretch to affix the band to the wrist of the user through the receiving loop and the first and second skin-contact portions are not configured to stretch.

(B2) In some embodiments of B1, the elastic material is at least 25% less in width than the first skin-contact portion of the band and the second skin-contact portion. In some embodiments, 50-75% of the width of the first skin-contact portion of the band is the minimum amount of surface area needed for the hook and loop structure to remain attached to a wearer's wrist while maintaining the required force to ensure a proper contact exists between the biopotential sensors and the user's wrist (e.g., enough force to ensure sensors are detecting signals without significant interference). For example, FIG. 2D shows that elastic band 224A and 224B are at least 25% less in width than the width of first skin contact portion 262A and a second skin contact portion 262B.

(B3) In some embodiments of B1-B2, the receiving loop and elastic material are configured such that stress applied to the receiving loop and elastic material are substantially not transferred to both the first flexible printed circuit board and the second flexible printed circuit board, when the wrist-wearable device is worn on a wrist of the user. For example, reinforcement plates 248A and 248B in FIG. 2C are configured to mitigate stress being applied to the flexible printed circuit boards 210A and 210B, respectively.

(B4) In some embodiments of any of B1-B3, the elastic material includes a loop (or a hook portion) portion of a hook and loop fastener, and the first skin-contact portion of the band includes a hook portion (or a loop portion) of the hook and loop fastener and is configured to attach with the loop portion after the elastic material has been passed through the receiving loop of the second skin-contact portion to secure the wrist-wearable device to a wrist of the user. For example, FIG. 2B shows that the elastic band 224A includes hook and loop portions 225.

(B5) In some embodiments of any of B1-B4, the first skin-contact portion of the band and the loop portion of the hook and loop fastener are sewn together (e.g., the rectangular portion of hook and loop portions 225 in FIG. 2B).

(B6) In some embodiments of any of B1-B5, the hook portion is sewn into the elastic material (e.g., the oval portions of hook and loop portions 225 in FIG. 2B).

(B7) In some embodiments of any of B1-B6, the hook portion of the hook and loop fastener is a distinct and separate material from the elastic material, and the hook portion of the hook and loop fastener is adhered to a top part of the first skin-contact portion, the top part being opposite to a bottom part of the first skin-contact portion at which the first set biopotential-signal sensors are coupled.

(B8) In some embodiments of any of B1-B7, elastic material and the receiving loop are attached through respective cutouts of the first and second skin-contact portions, and then adhered to those portions (e.g., FIG. 2B shows that a backside 217 of a textile 218 has two cutouts 220A and 220B that are configured to pass elastic bands 224A and 224B through them).

(B9) In some embodiments of any of B1-B8, a number of the first set of biopotential-signal sensors is larger than a number of the second set of biopotential-signal sensors (e.g., FIGS. 2A, 2C and 2D illustrate that biopotential sensors 204A-204J (i.e., 10 biopotential sensors) are part of first skin contact portion 262A and biopotential sensors 204K-204P (i.e., 6 biopotential sensors) are part of the second skin contact portion 262B).

(B10) In some embodiments of any of B1-B9, first skin-contact portion is longer than the second skin-contact portion (e.g., FIGS. 2A, 2C and 2D illustrate that first skin contact portion 262A is longer than second skin contact portion 262B).

(B11) In some embodiments of any of B1-B10, the first set of biopotential-signal sensors contains fewer biopotential-signal sensors than the second set of biopotential-signal sensors. In some embodiments, the second set of biopotential-signal sensors contains more biopotential-signal sensors than the second set of biopotential-signal sensors. In some embodiments, the number of biopotential-signal sensors correspond to areas with the most detectable information (e.g., more tendons, more nerves, more muscles).

(B12) In some embodiments of any of B1-B11, the first and second flexible printed circuit boards are directly adhered to the first and second skin-contact portions (e.g., FIG. 2C shows in manufacturing step 250 that first biopotential assembly 212A and second biopotential assembly 212B are directly coupled with the wrist-facing textile 238).

(B13) In some embodiments of any of B1-B12, the first skin-contact portion of the band and the second skin-contact portion of the band each include cutouts (e.g., in the shape of a biopotential signal sensor (e.g., undersized)) for the first set of biopotential-signal sensors and the second set of biopotential-signal sensors to pass-through, respectively (e.g., first set of cutouts 245A-245J and second set of cutouts 245K-245P shown in FIG. 2C are configured to receive 204A-204J biopotential sensors and biopotential sensors 204K-204P, respectively).

(B14) In some embodiments of any of B1-B13, contact points of the first and second flexible printed circuit boards are exposed for connection with a capsule portion, wherein the capsule portion connects to both the first and second flexible printed circuit boards. For example, FIGS. 2C and 2D show a connector portion of the first biopotential assembly 212A and a connector portion of the first biopotential assembly 212B being exposed and configured to connect with the capsule 270.

(B15) In some embodiments of any of B1-B14, the capsule portion connects to both the first and second flexible printed circuit boards via multiple fasteners and an adhesive (e.g., as described in reference to FIG. 2D, the capsule 270 is secured by one or more of: adhesive, screws into the reinforcement plates 248A and 248B, and press fittings).

(B16) In some embodiments of any of B1-B15, the elastic material is partially adhered to a top part of the first skin-contact portion.

(B17) In some embodiments of any of B1-B16, the elastic material is 3.5-5.5 inches in length.

(B18) In some embodiments of any of B1-B17, an end of the elastic material includes a portion that is folded over on itself and the folded over portion is between 4/16 and 6/16 of an inch.

(B19) In some embodiments of any of B1-B18, the elastic material includes a hook and loop portion that is 2.5-4.5 inches in length.

(B20) In some embodiments of any of B1-B19, the first skin-contact portion of the band is coupled with the elastic material via an adhesive.

(B21) In some embodiments of any of B1-B20, the first skin-contact portion of the band is coupled with the receiving loop via an adhesive.

(C1) In accordance with some embodiments, an artificial reality system includes a head worn device (e.g., with a display) and a wrist-wearable device configured to provide inputs to the head worn device, wherein the wrist-wearable device is configured in accordance with any of A1-A3 and B1-B21.

(D1) In accordance with some embodiments, a band (e.g., a wrist-worn band, head-worn band, ankle-worn band, a torso-worn band, etc.) comprises a first skin-contact portion of a band of the band that: (i) includes a first flexible printed circuit board, (ii) is coupled with a first set of biopotential-signal sensors for detecting first biopotential signals that are provided to the first flexible printed circuit board, and (iii) is coupled with an elastic material that extends beyond an end of the first skin-contact portion of the band. The band also comprises a second skin-contact portion of the band that is separated from the first skin-contact portion of the band by a capsule structure, the second skin-contact portion: (i) including a second flexible printed circuit board, (ii) coupled with a second set of biopotential-signal sensors for detecting biopotential signals that are provided to the second flexible printed circuit board, and (iii) coupled with a receiving loop for receiving the elastic material to affix the band to a body part of a wearer of the band. In some embodiments, the first skin-contact portion and the second skin-contact portion are made of a same material that is distinct from the elastic material, such that when the band is worn on the wrist of a user the elastic material is configured to stretch to affix the band to a wrist of the user through the receiving loop and the first and second skin-contact portions are not configured to stretch.

(D2) In some embodiments of D1, the band is configured in accordance with any of A1 through C1.

The devices described above are further detailed below, including wrist-wearable devices, headset devices, systems, and haptic feedback devices. Specific operations described above may occur as a result of specific hardware, such hardware is described in further detail below. The devices described below are not limiting and features on these devices can be removed or additional features can be added to these devices.

Example Wrist-Wearable Devices

Figure 4A:
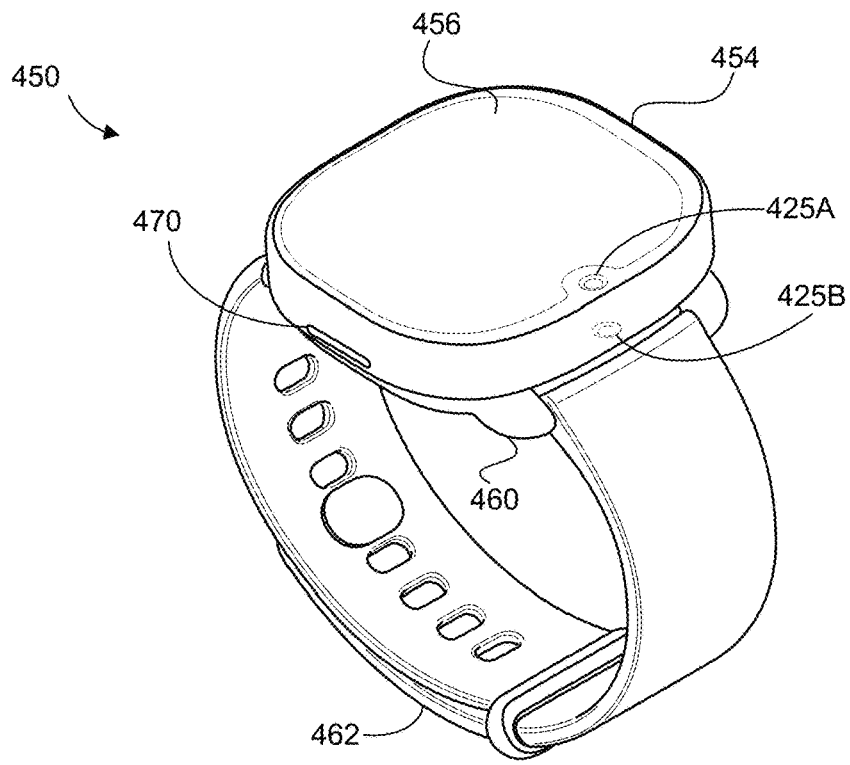
FIGS. 4A-4E illustrate an example wrist-wearable device, in accordance with some embodiments.
Figure 4A:
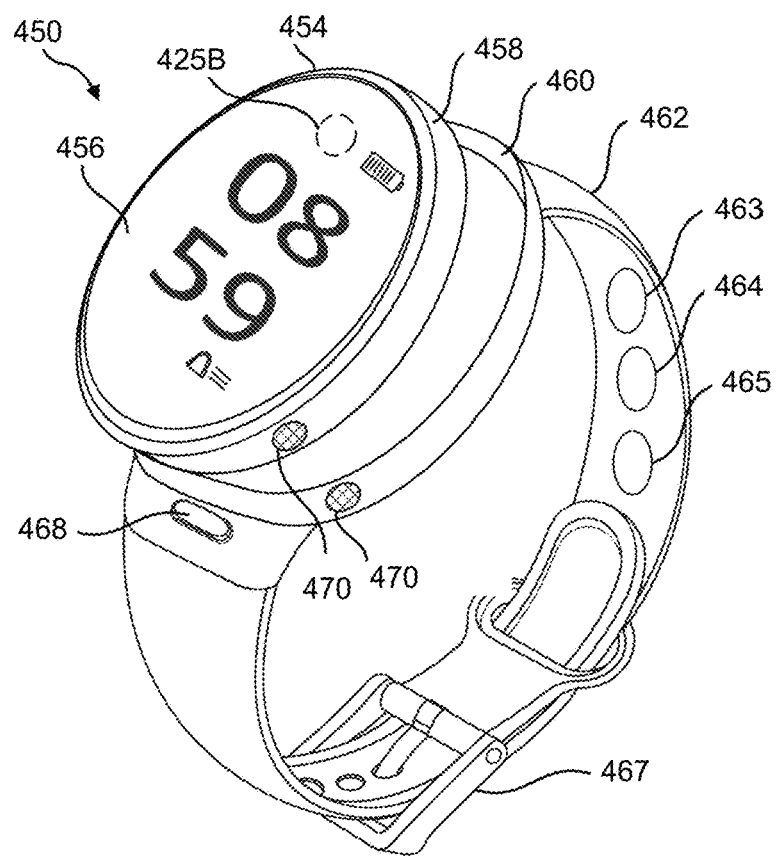
Figure 4B:
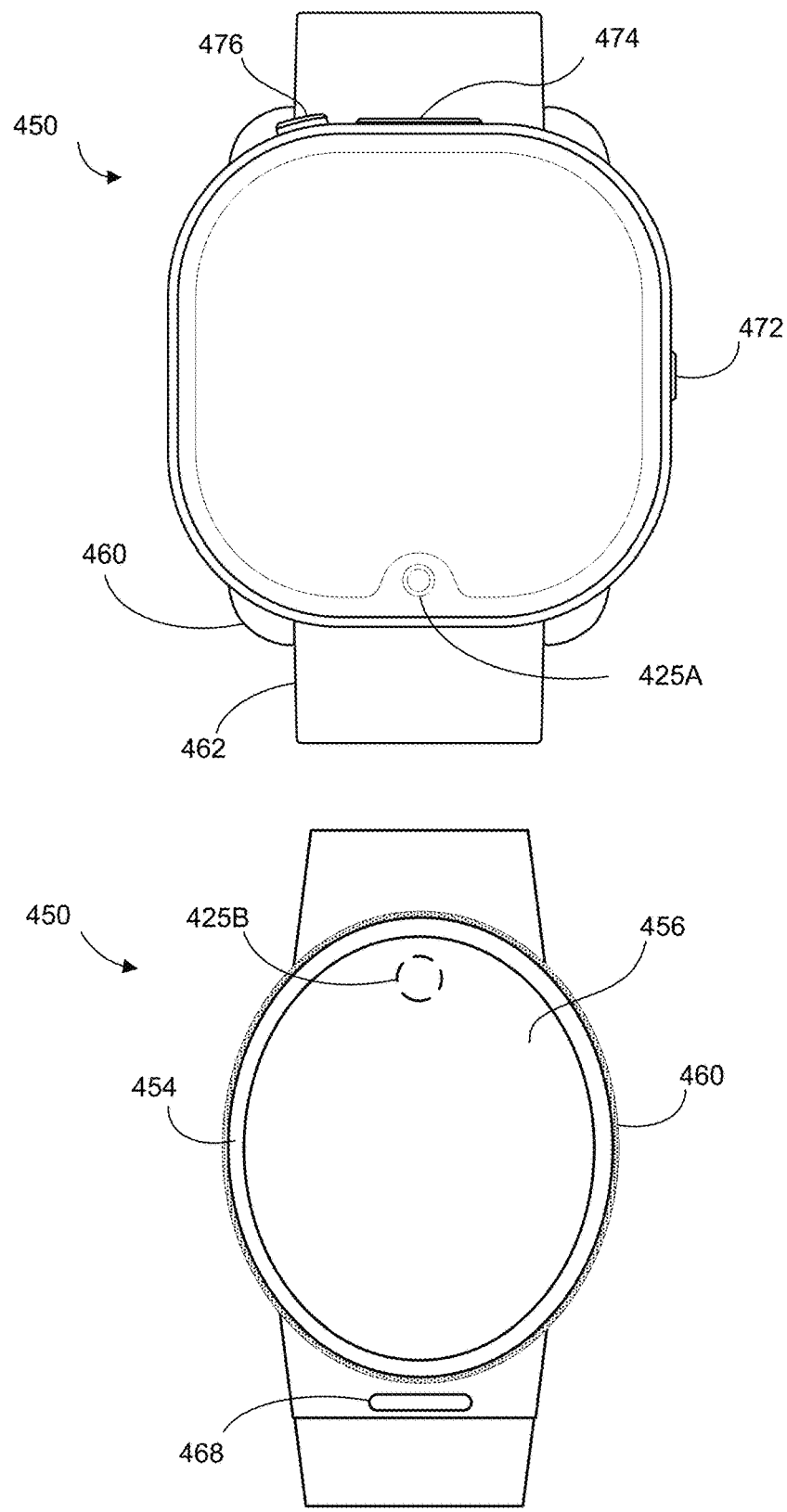

FIGS. 4A and 4B illustrate an example wrist-wearable device 450, in accordance with some embodiments. The wrist-wearable device 450 is an instance of the wearable device described herein, such that the wearable device should be understood to have the features of the wrist-wearable device 450 and vice versa. FIG. 4A illustrates a perspective view of the wrist-wearable device 450 that includes a watch body 454 coupled with a watch band 462. The watch body 454 and the watch band 462 can have a substantially rectangular or circular shape and can be configured to allow a user to wear the wrist-wearable device 450 on a body part (e.g., a wrist). The wrist-wearable device 450 can include a retaining mechanism 467 (e.g., a buckle, a hook and loop fastener, etc.) for securing the watch band 462 to the user's wrist. The wrist-wearable device 450 can also include a coupling mechanism 460 (e.g., a cradle) for detachably coupling the capsule or watch body 454 (via a coupling surface of the watch body 454) to the watch band 462.

The wrist-wearable device 450 can perform various functions associated with navigating through user interfaces and selectively opening applications. As will be described in more detail below, operations executed by the wrist-wearable device 450 can include, without limitation, display of visual content to the user (e.g., visual content displayed on display 456); sensing user input (e.g., sensing a touch on peripheral button 468, sensing biometric data on sensor 464, sensing neuromuscular signals on neuromuscular sensor 465, etc.); messaging (e.g., text, speech, video, etc.); image capture; wireless communications (e.g., cellular, near field, Wi-Fi, personal area network, etc.); location determination; financial transactions; providing haptic feedback; alarms; notifications; biometric authentication; health monitoring; sleep monitoring; etc. These functions can be executed independently in the watch body 454, independently in the watch band 462, and/or in communication between the watch body 454 and the watch band 462. In some embodiments, functions can be executed on the wrist-wearable device 450 in conjunction with an artificial-reality environment that includes, but is not limited to, virtual-reality (VR) environments (including non-immersive, semi-immersive, and fully immersive VR environments); augmented-reality environments (including marker-based augmented-reality environments, markerless augmented-reality environments, location-based augmented-reality environments, and projection-based augmented-reality environments); hybrid reality; and other types of mixed-reality environments. As the skilled artisan will appreciate upon reading the descriptions provided herein, the novel wearable devices described herein can be used with any of these types of artificial-reality environments.

The watch band 462 can be configured to be worn by a user such that an inner surface of the watch band 462 is in contact with the user's skin. When worn by a user, sensor 464 is in contact with the user's skin. The sensor 464 can be a biosensor that senses a user's heart rate, saturated oxygen level, temperature, sweat level, muscle intentions, or a combination thereof. The watch band 462 can include multiple sensors 464 that can be distributed on an inside and/or an outside surface of the watch band 462. Additionally, or alternatively, the watch body 454 can include sensors that are the same or different than those of the watch band 462 (or the watch band 462 can include no sensors at all in some embodiments). For example, multiple sensors can be distributed on an inside and/or an outside surface of the watch body 454. As described below with reference to FIGS. 4B and/or 4C, the watch body 454 can include, without limitation, a front-facing image sensor 425A and/or a rear-facing image sensor 425B, a biometric sensor, an IMU, a heart rate sensor, a saturated oxygen sensor, a neuromuscular sensor (s), an altimeter sensor, a temperature sensor, a bioimpedance sensor, a pedometer sensor, an optical sensor (e.g., imaging sensor 4104), a touch sensor, a sweat sensor, etc. The sensor 464 can also include a sensor that provides data about a user's environment including a user's motion (e.g., an IMU), altitude, location, orientation, gait, or a combination thereof. The sensor 464 can also include a light sensor (e.g., an infrared light sensor, a visible light sensor) that is configured to track a position and/or motion of the watch body 454 and/or the watch band 462. The watch band 462 can transmit the data acquired by sensor 464 to the watch body 454 using a wired communication method (e.g., a Universal Asynchronous Receiver/Transmitter (UART), a USB transceiver, etc.) and/or a wireless communication method (e.g., near field communication, Bluetooth, etc.). The watch band 462 can be configured to operate (e.g., to collect data using sensor 464) independent of whether the watch body 454 is coupled to or decoupled from watch band 462.

In some examples, the watch band 462 can include a neuromuscular sensor 465 (e.g., an EMG sensor, a mechanomyogram (MMG) sensor, a sonomyography (SMG) sensor, etc.). Neuromuscular sensor 465 can sense a user's intention to perform certain motor actions. The sensed muscle intention can be used to control certain user interfaces displayed on the display 456 of the wrist-wearable device 450 and/or can be transmitted to a device responsible for rendering an artificial-reality environment (e.g., a head-mounted display) to perform an action in an associated artificial-reality environment, such as to control the motion of a virtual device displayed to the user.

Signals from neuromuscular sensor 465 can be used to provide a user with an enhanced interaction with a physical object and/or a virtual object in an artificial-reality application generated by an artificial-reality system (e.g., user interface objects presented on the display 456, or another computing device (e.g., a smartphone)). Signals from neuromuscular sensor 465 can be obtained (e.g., sensed and recorded) by one or more neuromuscular sensors 465 of the watch band 462. Although FIG. 4A shows one neuromuscular sensor 465, the watch band 462 can include a plurality of neuromuscular sensors 465 arranged circumferentially on an inside surface of the watch band 462 such that the plurality of neuromuscular sensors 465 contact the skin of the user. The watch band 462 can include a plurality of neuromuscular sensors 465 arranged circumferentially on an inside surface of the watch band 462. Neuromuscular sensor 465 can sense and record neuromuscular signals from the user as the user performs muscular activations (e.g., movements, gestures, etc.). The muscular activations performed by the user can include static gestures, such as placing the user's hand palm down on a table; dynamic gestures, such as grasping a physical or virtual object; and covert gestures that are imperceptible to another person, such as slightly tensing a joint by co-contracting opposing muscles or using sub-muscular activations. The muscular activations performed by the user can include symbolic gestures (e.g., gestures mapped to other gestures, interactions, or commands, for example, based on a gesture vocabulary that specifies the mapping of gestures to commands).

The watch band 462 and/or watch body 454 can include a haptic device 463 (e.g., a vibratory haptic actuator) that is configured to provide haptic feedback (e.g., a cutaneous and/or kinesthetic sensation, etc.) to the user's skin. The sensors 464 and 465, and/or the haptic device 463 can be configured to operate in conjunction with multiple applications including, without limitation, health monitoring, social media, game playing, and artificial reality (e.g., the applications associated with artificial reality).

The wrist-wearable device 450 can include a coupling mechanism (also referred to as a cradle) for detachably coupling the watch body 454 to the watch band 462. A user can detach the watch body 454 from the watch band 462 in order to reduce the encumbrance of the wrist-wearable device 450 to the user. The wrist-wearable device 450 can include a coupling surface on the watch body 454 and/or coupling mechanism(s) 460 (e.g., a cradle, a tracker band, a support base, a clasp). A user can perform any type of motion to couple the watch body 454 to the watch band 462 and to decouple the watch body 454 from the watch band 462. For example, a user can twist, slide, turn, push, pull, or rotate the watch body 454 relative to the watch band 462, or a combination thereof, to attach the watch body 454 to the watch band 462 and to detach the watch body 454 from the watch band 462.

As shown in the example of FIG. 4A, the watch band coupling mechanism 460 can include a type of frame or shell that allows the watch body 454 coupling surface to be retained within the watch band coupling mechanism 460. The watch body 454 can be detachably coupled to the watch band 462 through a friction fit, magnetic coupling, a rotation-based connector, a shear-pin coupler, a retention spring, one or more magnets, a clip, a pin shaft, a hook and loop fastener, or a combination thereof. In some examples, the watch body 454 can be decoupled from the watch band 462 by actuation of the release mechanism 470. The release mechanism 470 can include, without limitation, a button, a knob, a plunger, a handle, a lever, a fastener, a clasp, a dial, a latch, or a combination thereof.

As shown in FIGS. 4A-4B, the coupling mechanism 460 can be configured to receive a coupling surface proximate to the bottom side of the watch body 454 (e.g., a side opposite to a front side of the watch body 454 where the display 456 is located), such that a user can push the watch body 454 downward into the coupling mechanism 460 to attach the watch body 454 to the coupling mechanism 460. In some embodiments, the coupling mechanism 460 can be configured to receive a top side of the watch body 454 (e.g., a side proximate to the front side of the watch body 454 where the display 456 is located) that is pushed upward into the cradle, as opposed to being pushed downward into the coupling mechanism 460. In some embodiments, the coupling mechanism 460 is an integrated component of the watch band 462 such that the watch band 462 and the coupling mechanism 460 are a single unitary structure.

The wrist-wearable device 450 can include a single release mechanism 470 or multiple release mechanisms 470 (e.g., two release mechanisms 470 positioned on opposing sides of the wrist-wearable device 450 such as spring-loaded buttons). As shown in FIG. 4A, the release mechanism 470 can be positioned on the watch body 454 and/or the watch band coupling mechanism 460. Although FIG. 4A shows release mechanism 470 positioned at a corner of watch body 454 and at a corner of watch band coupling mechanism 460, the release mechanism 470 can be positioned anywhere on watch body 454 and/or watch band coupling mechanism 460 that is convenient for a user of wrist-wearable device 450 to actuate. A user of the wrist-wearable device 450 can actuate the release mechanism 470 by pushing, turning, lifting, depressing, shifting, or performing other actions on the release mechanism 470. Actuation of the release mechanism 470 can release (e.g., decouple) the watch body 454 from the watch band coupling mechanism 460 and the watch band 462 allowing the user to use the watch body 454 independently from watch band 462. For example, decoupling the watch body 454 from the watch band 462 can allow the user to capture images using rear-facing image sensor 425B.

FIG. 4B includes top views of examples of the wrist-wearable device 450. The examples of the wrist-wearable device 450 shown in FIGS. 4A-4B can include a coupling mechanism 460 (as shown in FIG. 4B, the shape of the coupling mechanism can correspond to the shape of the watch body 454 of the wrist-wearable device 450). The watch body 454 can be detachably coupled to the coupling mechanism 460 through a friction fit, magnetic coupling, a rotation-based connector, a shear-pin coupler, a retention spring, one or more magnets, a clip, a pin shaft, a hook and loop fastener, or any combination thereof.

In some examples, the watch body 454 can be decoupled from the coupling mechanism 460 by actuation of a release mechanism 470. The release mechanism 470 can include, without limitation, a button, a knob, a plunger, a handle, a lever, a fastener, a clasp, a dial, a latch, or a combination thereof. In some examples, the wristband system functions can be executed independently in the watch body 454, independently in the coupling mechanism 460, and/or in communication between the watch body 454 and the coupling mechanism 460. The coupling mechanism 460 can be configured to operate independently (e.g., execute functions independently) from watch body 454. Additionally, or alternatively, the watch body 454 can be configured to operate independently (e.g., execute functions independently) from the coupling mechanism 460. As described below with reference to the block diagram of FIG. 4A, the coupling mechanism 460 and/or the watch body 454 can each include the independent resources required to independently execute functions. For example, the coupling mechanism 460 and/or the watch body 454 can each include a power source (e.g., a battery), a memory, data storage, a processor (e.g., a central processing unit (CPU)), communications, a light source, and/or input/output devices.

The wrist-wearable device 450 can have various peripheral buttons 472, 474, and 476, for performing various operations at the wrist-wearable device 450. Also, various sensors, including one or both of the sensors 464 and 465, can be located on the bottom of the watch body 454, and can optionally be used even when the watch body 454 is detached from the watch band 462.

Figure 4C:
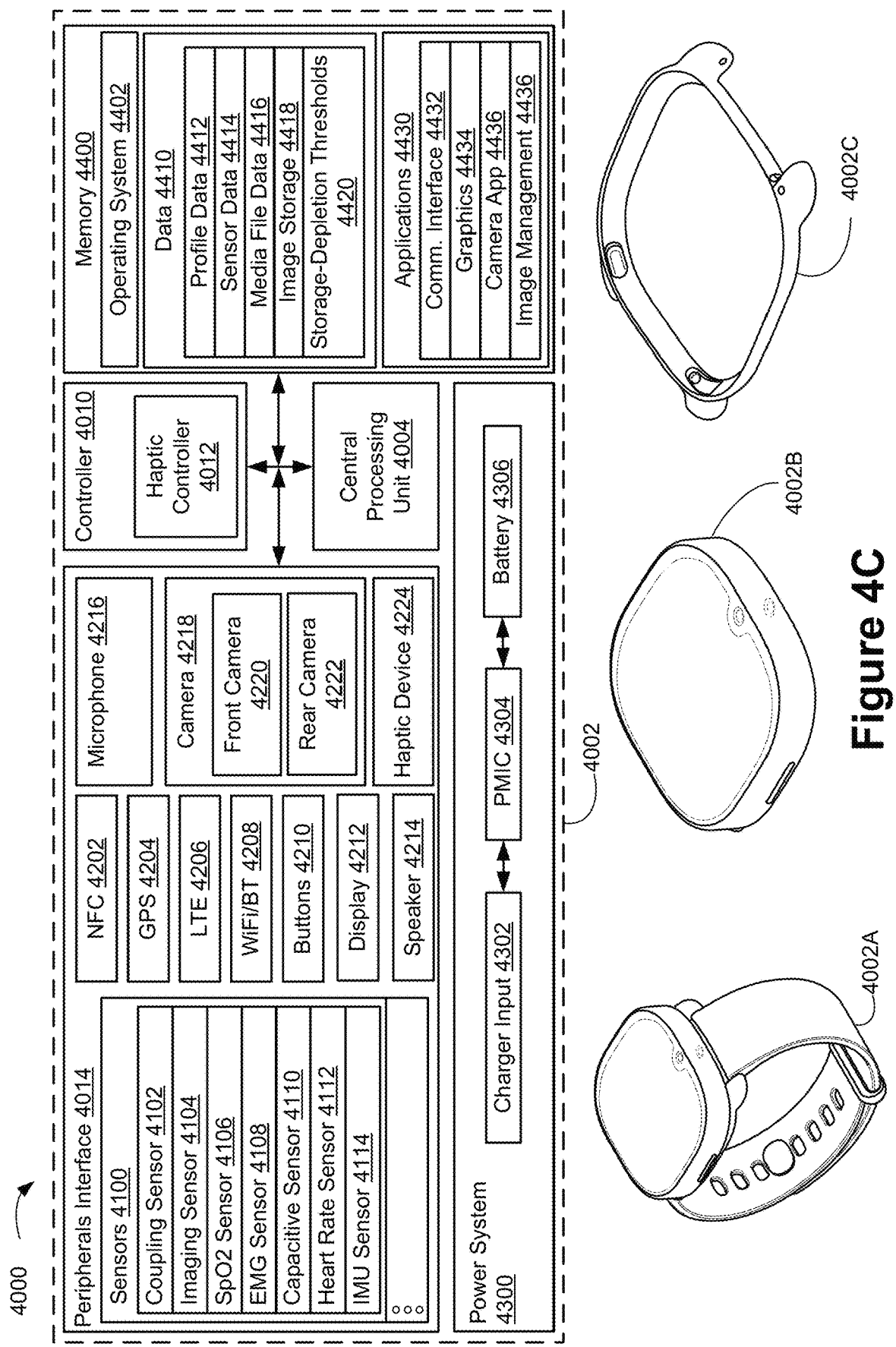

FIG. 4C is a block diagram of a computing system 4000, according to at least one embodiment of the present disclosure. The computing system 4000 includes an electronic device 4002, which can be, for example, a wrist-wearable device. The wrist-wearable device 450 described in detail above with respect to FIGS. 4A-4B is an example of the electronic device 4002, so the electronic device 4002 will be understood to include the components shown and described below for the computing system 4000. In some embodiments, all, or a substantial portion of the components of the computing system 4000 are included in a single integrated circuit. In some embodiments, the computing system 4000 can have a split architecture (e.g., a split mechanical architecture, a split electrical architecture) between a watch body (e.g., a watch body 454 in FIGS. 4A-4B) and a watch band (e.g., a watch band 462 in FIGS. 4A-4B). The electronic device 4002 can include a processor (e.g., a central processing unit 4004), a controller 4010, a peripherals interface 4014 that includes one or more sensors 4100 and various peripheral devices, a power source (e.g., a power system 4300), and memory (e.g., a memory 4400) that includes an operating system (e.g., an operating system 4402), data (e.g., data 4410), and one or more applications (e.g., applications 4430).

In some embodiments, the computing system 4000 includes the power system 4300 which includes a charger input 4302, a power-management integrated circuit (PMIC) 4304, and a battery 4306.

In some embodiments, a watch body and a watch band can each be electronic devices 4002 that each have respective batteries (e.g., battery 4306), and can share power with each other. The watch body and the watch band can receive a charge using a variety of techniques. In some embodiments, the watch body and the watch band can use a wired charging assembly (e.g., power cords) to receive the charge. Alternatively, or in addition, the watch body and/or the watch band can be configured for wireless charging. For example, a portable charging device can be designed to mate with a portion of watch body and/or watch band and wirelessly deliver usable power to a battery of watch body and/or watch band.

The watch body and the watch band can have independent power systems 4300 to enable each to operate independently. The watch body and watch band can also share power (e.g., one can charge the other) via respective PMICs 4304 that can share power over power and ground conductors and/or over wireless charging antennas.

In some embodiments, the peripherals interface 4014 can include one or more sensors 4100. The sensors 4100 can include a coupling sensor 4102 for detecting when the electronic device 4002 is coupled with another electronic device 4002 (e.g., a watch body can detect when it is coupled to a watch band, and vice versa). The sensors 4100 can include imaging sensors 4104 for collecting imaging data, which can optionally be the same device as one or more of the cameras 4218. In some embodiments, the imaging sensors 4104 can be separate from the cameras 4218. In some embodiments the sensors include an SpO2 sensor 4106. In some embodiments, the sensors 4100 include an EMG sensor 4108 for detecting, for example muscular movements by a user of the electronic device 4002. In some embodiments, the sensors 4100 include a capacitive sensor 4110 for detecting changes in potential of a portion of a user's body. In some embodiments, the sensors 4100 include a heart rate sensor 4112. In some embodiments, the sensors 5100 include an inertial measurement unit (IMU) sensor 4114 for detecting, for example, changes in acceleration of the user's hand.

In some embodiments, the peripherals interface 4014 includes a near-field communication (NFC) component 4202, a global-position system (GPS) component 4204, a long-term evolution (LTE) component 4206, and or a Wi-Fi or Bluetooth communication component 4208.

In some embodiments, the peripherals interface includes one or more buttons (e.g., the peripheral buttons 457, 458, and 459 in FIG. 4B), which, when selected by a user, cause operation to be performed at the electronic device 4002.

The electronic device 4002 can include at least one display 4212, for displaying visual affordances to the user, including user-interface elements and/or three-dimensional virtual objects. The display can also include a touch screen for inputting user inputs, such as touch gestures, swipe gestures, and the like.

The electronic device 4002 can include at least one speaker 4214 and at least one microphone 4216 for providing audio signals to the user and receiving audio input from the user. The user can provide user inputs through the microphone 4216 and can also receive audio output from the speaker 4214 as part of a haptic event provided by the haptic controller 4012.

The electronic device 4002 can include at least one camera 4218, including a front camera 4220 and a rear camera 4222. In some embodiments, the electronic device 4002 can be a head-wearable device, and one of the cameras 4218 can be integrated with a lens assembly of the head-wearable device.

One or more of the electronic devices 4002 can include one or more haptic controllers 4012 and associated componentry for providing haptic events at one or more of the electronic devices 4002 (e.g., a vibrating sensation or audio output in response to an event at the electronic device 4002). The haptic controllers 4012 can communicate with one or more electroacoustic devices, including a speaker of the one or more speakers 4214 and/or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). The haptic controller 4012 can provide haptic events to that are capable of being sensed by a user of the electronic devices 4002. In some embodiments, the one or more haptic controllers 4012 can receive input signals from an application of the applications 4430.

Memory 4400 optionally includes high-speed random-access memory and optionally also includes non-volatile memory, such as one or more magnetic disk storage devices, flash memory devices, or other non-volatile solid-state memory devices. Access to the memory 4400 by other components of the electronic device 4002, such as the one or more processors of the central processing unit 4004, and the peripherals interface 4014 is optionally controlled by a memory controller of the controllers 4010.

In some embodiments, software components stored in the memory 4400 can include one or more operating systems 4402 (e.g., a Linux-based operating system, an Android operating system, etc.). The memory 4400 can also include data 4410, including structured data (e.g., SQL databases, MongoDB databases, GraphQL data, JSON data, etc.). The data 4410 can include profile data 4412, sensor data 4414, media file data 4414.

In some embodiments, software components stored in the memory 4400 include one or more applications 4430 configured to be perform operations at the electronic devices 4002. In some embodiments, the one or more applications 4430 include one or more communication interface modules 4432, one or more graphics modules 4434, one or more camera application modules 4436. In some embodiments, a plurality of applications 4430 can work in conjunction with one another to perform various tasks at one or more of the electronic devices 4002.

It should be appreciated that the electronic devices 4002 are only some examples of the electronic devices 4002 within the computing system 4000, and that other electronic devices 4002 that are part of the computing system 4000 can have more or fewer components than shown optionally combines two or more components, or optionally have a different configuration or arrangement of the components. The various components shown in FIG. 4C are implemented in hardware, software, firmware, or a combination thereof, including one or more signal processing and/or application-specific integrated circuits.

As illustrated by the lower portion of FIG. 4C, various individual components of a wrist-wearable device can be examples of the electronic device 4002. For example, some or all of the components shown in the electronic device 4002 can be housed or otherwise disposed in a combined watch device 4002A, or within individual components of the capsule device watch body 4002B, the cradle portion 4002C, and/or a watch band.

Figure 4D:
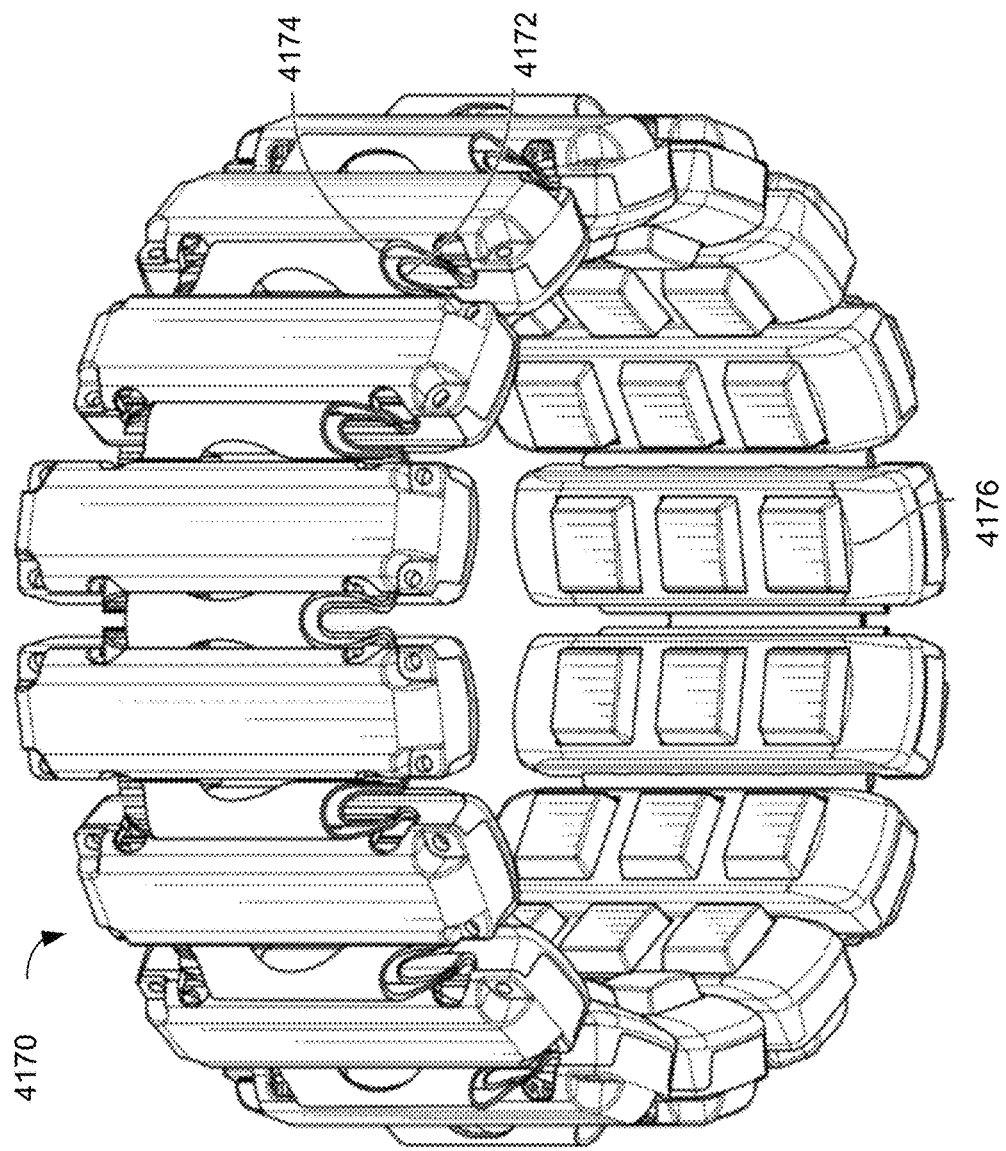

FIG. 4D illustrates a wearable device 4170, in accordance with some embodiments. In some embodiments, the wearable device 4170 is used to generate control information (e.g., sensed data about neuromuscular signals or instructions to perform certain commands after the data is sensed) for causing a computing device to perform one or more input commands. In some embodiments, the wearable device 4170 includes a plurality of neuromuscular sensors 4176. In some embodiments, the plurality of neuromuscular sensors 4176 includes a predetermined number of (e.g., 16) neuromuscular sensors (e.g., EMG sensors) arranged circumferentially around an elastic band 4174. The plurality of neuromuscular sensors 4176 may include any suitable number of neuromuscular sensors. In some embodiments, the number and arrangement of neuromuscular sensors 4176 depends on the particular application for which the wearable device 4170 is used. For instance, a wearable device 4170 configured as an armband, wristband, or chest-band may include a plurality of neuromuscular sensors 4176 with different number of neuromuscular sensors and different arrangement for each use case, such as medical use cases as compared to gaming or general day-to-day use cases. For example, at least 16 neuromuscular sensors 4176 may be arranged circumferentially around elastic band 4174.

In some embodiments, the elastic band 4174 is configured to be worn around a user's lower arm or wrist. The elastic band 4174 may include a flexible electronic connector 4172. In some embodiments, the flexible electronic connector 4172 interconnects separate sensors and electronic circuitry that are enclosed in one or more sensor housings. Alternatively, in some embodiments, the flexible electronic connector 4172 interconnects separate sensors and electronic circuitry that are outside of the one or more sensor housings. Each neuromuscular sensor of the plurality of neuromuscular sensors 4176 can include a skin-contacting surface that includes one or more electrodes. One or more sensors of the plurality of neuromuscular sensors 4176 can be coupled together using flexible electronics incorporated into the wearable device 4170. In some embodiments, one or more sensors of the plurality of neuromuscular sensors 4176 can be integrated into a woven fabric, wherein the fabric one or more sensors of the plurality of neuromuscular sensors 4176 are sewn into the fabric and mimic the pliability of fabric (e.g., the one or more sensors of the plurality of neuromuscular sensors 4176 can be constructed from a series woven strands of fabric). In some embodiments, the sensors are flush with the surface of the textile and are indistinguishable from the textile when worn by the user.

Figure 4E:
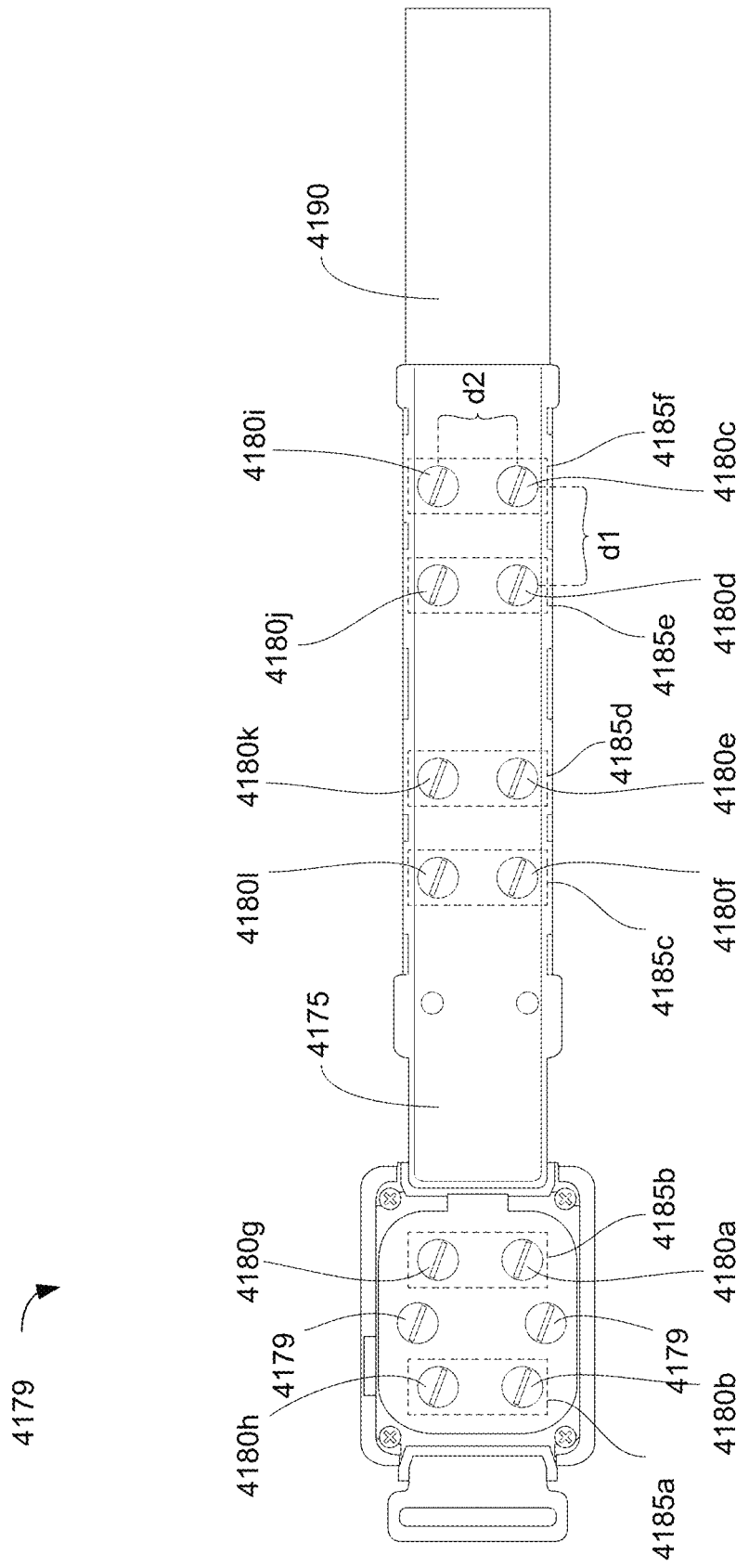

FIG. 4E illustrates a wearable device 4179 in accordance with some embodiments. The wearable device 4179 includes paired sensor channels 4185a-4185f along an interior surface of a wearable structure 4175 that are configured to detect neuromuscular signals. Different number of paired sensors channels can be used (e.g., one pair of sensors, three pairs of sensors, four pairs of sensors, or six pairs of sensors). The wearable structure 4175 can include a band portion 4190, a capsule portion 4195, and a cradle portion (not pictured) that is coupled with the band portion 4190 to allow for the capsule portion 4195 to be removably coupled with the band portion 4190. For embodiments in which the capsule portion 4195 is removable, the capsule portion 4195 can be referred to as a removable structure, such that in these embodiments the wearable device includes a wearable portion (e.g., band portion 4190 and the cradle portion) and a removable structure (the removable capsule portion which can be removed from the cradle). In some embodiments, the capsule portion 4195 includes the one or more processors and/or other components of the wearable device 688 described above in reference to FIGS. 6A and 6B. The wearable structure 4175 is configured to be worn by a user 611. More specifically, the wearable structure 4175 is configured to couple the wearable device 4179 to a wrist, arm, forearm, or other portion of the user's body. Each paired sensor channels 4185a-4185f includes two electrodes 4180 (e.g., electrodes 4180a-4180h) for sensing neuromuscular signals based on differential sensing within each respective sensor channel. In accordance with some embodiments, the wearable device 4170 further includes an electrical ground and a shielding electrode.

The techniques described above can be used with any device for sensing neuromuscular signals, including the arm-wearable devices of FIG. 4A-4C, but could also be used with other types of wearable devices for sensing neuromuscular signals (such as body-wearable or head-wearable devices that might have neuromuscular sensors closer to the brain or spinal column).

In some embodiments, a wrist-wearable device can be used in conjunction with a head-wearable device described below, and the wrist-wearable device can also be configured to be used to allow a user to control aspect of the artificial reality (e.g., by using EMG-based gestures to control user interface objects in the artificial reality and/or by allowing a user to interact with the touchscreen on the wrist-wearable device to also control aspects of the artificial reality). Having thus described example wrist-wearable device, attention will now be turned to example head-wearable devices, such AR glasses and VR headsets.

Example Head-Wearable Devices

Figure 5A:
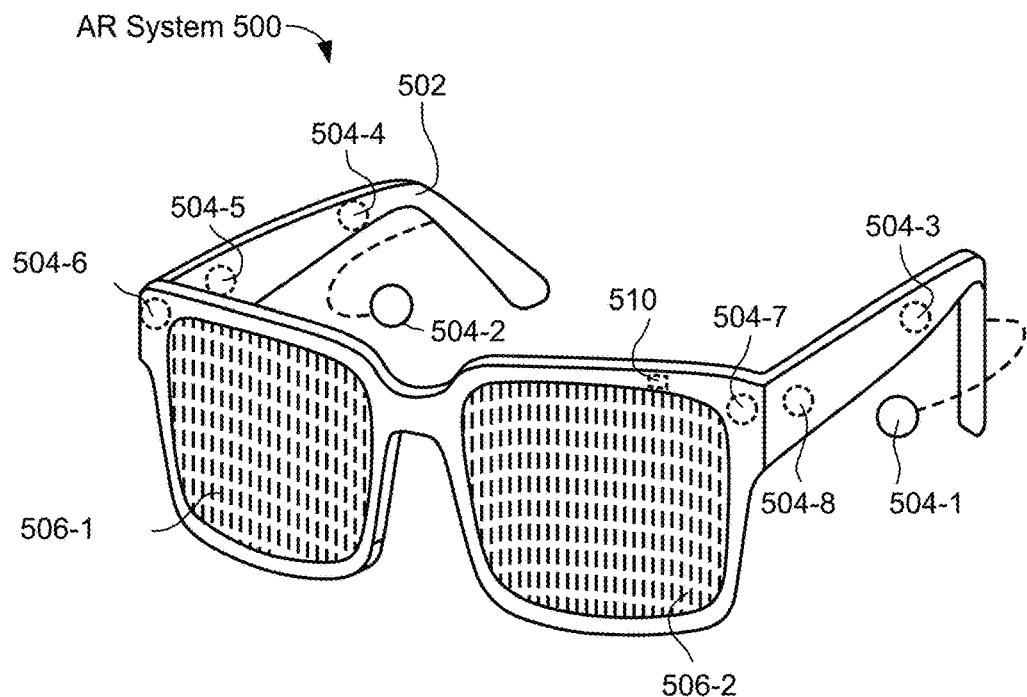
FIGS. 5A-5B illustrate an example AR system in accordance with some embodiments.

FIG. 5A shows an example AR system 500 in accordance with some embodiments. In FIG. 5A, the AR system 500 includes an eyewear device with a frame 502 configured to hold a left display device 506-1 and a right display device 506-2 in front of a user's eyes. The display devices 506-1 and 506-2 may act together or independently to present an image or series of images to a user. While the AR system 500 includes two displays, embodiments of this disclosure may be implemented in AR systems with a single near-eye display (NED) or more than two NEDs.

In some embodiments, the AR system 500 includes one or more sensors, such as the acoustic sensors 504. For example, the acoustic sensors 504 can generate measurement signals in response to motion of the AR system 500 and may be located on substantially any portion of the frame 502. Any one of the sensors may be a position sensor, an IMU, a depth camera assembly, or any combination thereof. In some embodiments, the AR system 500 includes more or fewer sensors than are shown in FIG. 5A. In embodiments in which the sensors include an IMU, the IMU may generate calibration data based on measurement signals from the sensors. Examples of the sensors include, without limitation, accelerometers, gyroscopes, magnetometers, other suitable types of sensors that detect motion, sensors used for error correction of the IMU, or some combination thereof.

In some embodiments, the AR system 500 includes a microphone array with a plurality of acoustic sensors 504-1 through 504-8, referred to collectively as the acoustic sensors 504. The acoustic sensors 504 may be transducers that detect air pressure variations induced by sound waves. In some embodiments, each acoustic sensor 504 is configured to detect sound and convert the detected sound into an electronic format (e.g., an analog or digital format). In some embodiments, the microphone array includes ten acoustic sensors: 504-1 and 504-2 designed to be placed inside a corresponding car of the user, acoustic sensors 504-3, 504-4, 504-5, 504-6, 504-7, and 504-8 positioned at various locations on the frame 502, and acoustic sensors positioned on a corresponding neckband, where the neckband is an optional component of the system that is not present in certain embodiments of the artificial-reality systems discussed herein.

The configuration of the acoustic sensors 504 of the microphone array may vary. While the AR system 500 is shown in FIG. 5A having ten acoustic sensors 504, the number of acoustic sensors 504 may be more or fewer than ten. In some situations, using more acoustic sensors 504 increases the amount of audio information collected and/or the sensitivity and accuracy of the audio information. In contrast, in some situations, using a lower number of acoustic sensors 504 decreases the computing power required by a controller to process the collected audio information. In addition, the position of each acoustic sensor 504 of the microphone array may vary. For example, the position of an acoustic sensor 504 may include a defined position on the user, a defined coordinate on the frame 502, an orientation associated with each acoustic sensor, or some combination thereof.

The acoustic sensors 504-1 and 504-2 may be positioned on different parts of the user's ear. In some embodiments, there are additional acoustic sensors on or surrounding the car in addition to acoustic sensors 504 inside the car canal. In some situations, having an acoustic sensor positioned next to an ear canal of a user enables the microphone array to collect information on how sounds arrive at the car canal. By positioning at least two of the acoustic sensors 504 on either side of a user's head (e.g., as binaural microphones), the AR device 500 is able to simulate binaural hearing and capture a 3D stereo sound field around a user's head. In some embodiments, the acoustic sensors 504-1 and 504-2 are connected to the AR system 500 via a wired connection, and in other embodiments, the acoustic sensors 504-1 and 504-2 are connected to the AR system 500 via a wireless connection (e.g., a Bluetooth connection). In some embodiments, the AR system 500 does not include the acoustic sensors 504-1 and 504-2.

The acoustic sensors 504 on the frame 502 may be positioned along the length of the temples, across the bridge of the nose, above or below the display devices 506, or in some combination thereof. The acoustic sensors 504 may be oriented such that the microphone array is able to detect sounds in a wide range of directions surrounding the user that is wearing the AR system 500. In some embodiments, a calibration process is performed during manufacturing of the AR system 500 to determine relative positioning of each acoustic sensor 504 in the microphone array.

In some embodiments, the eyewear device further includes, or is communicatively coupled to, an external device (e.g., a paired device), such as the optional neckband discussed above. In some embodiments, the optional neckband is coupled to the eyewear device via one or more connectors. The connectors may be wired or wireless connectors and may include electrical and/or non-electrical (e.g., structural) components. In some embodiments, the eyewear device and the neckband operate independently without any wired or wireless connection between them. In some embodiments, the components of the eyewear device and the neckband are located on one or more additional peripheral devices paired with the eyewear device, the neckband, or some combination thereof. Furthermore, the neckband is intended to represent any suitable type or form of paired device. Thus, the following discussion of neckband may also apply to various other paired devices, such as smart watches, smart phones, wrist bands, other wearable devices, hand-held controllers, tablet computers, or laptop computers.

In some situations, pairing external devices, such as the optional neckband, with the AR eyewear device enables the AR eyewear device to achieve the form factor of a pair of glasses while still providing sufficient battery and computation power for expanded capabilities. Some, or all, of the battery power, computational resources, and/or additional features of the AR system 500 may be provided by a paired device or shared between a paired device and an eyewear device, thus reducing the weight, heat profile, and form factor of the eyewear device overall while still retaining desired functionality. For example, the neckband may allow components that would otherwise be included on an eyewear device to be included in the neckband thereby shifting a weight load from a user's head to a user's shoulders. In some embodiments, the neckband has a larger surface area over which to diffuse and disperse heat to the ambient environment. Thus, the neckband may allow for greater battery and computation capacity than might otherwise have been possible on a stand-alone eyewear device. Because weight carried in the neckband may be less invasive to a user than weight carried in the eyewear device, a user may tolerate wearing a lighter eyewear device and carrying or wearing the paired device for greater lengths of time than the user would tolerate wearing a heavy, stand-alone eyewear device, thereby enabling an artificial-reality environment to be incorporated more fully into a user's day-to-day activities.

In some embodiments, the optional neckband is communicatively coupled with the eyewear device and/or to other devices. The other devices may provide certain functions (e.g., tracking, localizing, depth mapping, processing, storage, etc.) to the AR system 500. In some embodiments, the neckband includes a controller and a power source. In some embodiments, the acoustic sensors of the neckband are configured to detect sound and convert the detected sound into an electronic format (analog or digital).

The controller of the neckband processes information generated by the sensors on the neckband and/or the AR system 500. For example, the controller may process information from the acoustic sensors 504. For each detected sound, the controller may perform a direction of arrival (DOA) estimation to estimate a direction from which the detected sound arrived at the microphone array. As the microphone array detects sounds, the controller may populate an audio data set with the information. In embodiments in which the AR system 500 includes an IMU, the controller may compute all inertial and spatial calculations from the IMU located on the eyewear device. The connector may convey information between the eyewear device and the neckband and between the eyewear device and the controller. The information may be in the form of optical data, electrical data, wireless data, or any other transmittable data form. Moving the processing of information generated by the eyewear device to the neckband may reduce weight and heat in the eyewear device, making it more comfortable and safer for a user.

In some embodiments, the power source in the neckband provides power to the eyewear device and the neckband. The power source may include, without limitation, lithium-ion batteries, lithium-polymer batteries, primary lithium batteries, alkaline batteries, or any other form of power storage. In some embodiments, the power source is a wired power source.

As noted, some artificial-reality systems may, instead of blending an artificial reality with actual reality, substantially replace one or more of a user's sensory perceptions of the real world with a virtual experience. One example of this type of system is a head-worn display system, such as the VR system 550 in FIG. 5B, which mostly or completely covers a user's field of view.

Figure 5B:
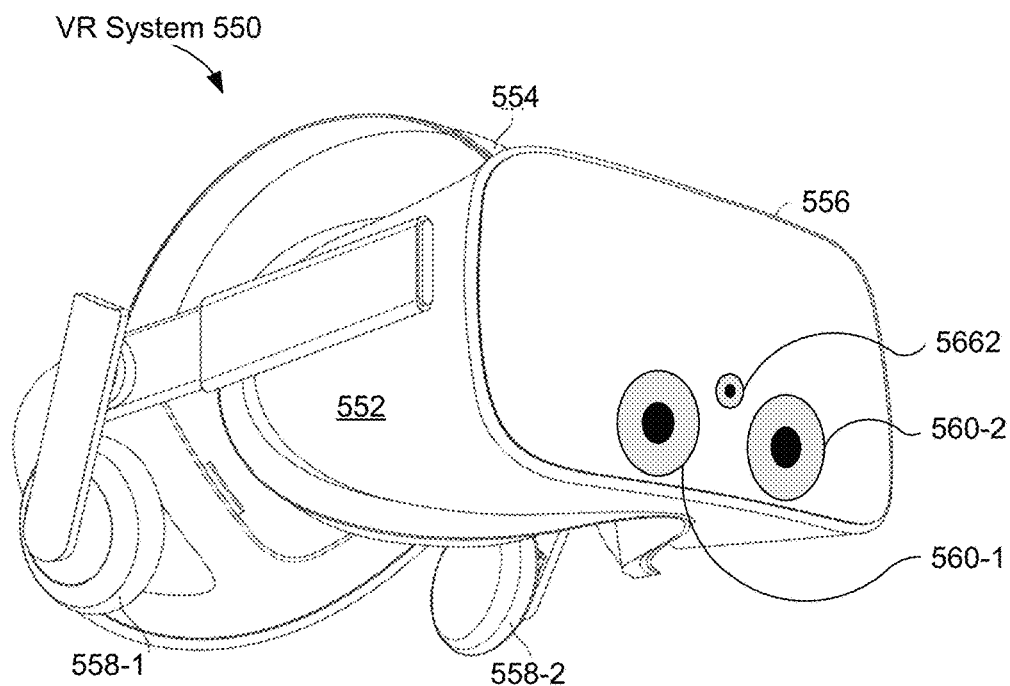

FIG. 5B shows a VR system 550 (e.g., also referred to herein as VR headsets or VR headset) in accordance with some embodiments. The VR system 550 includes a head-mounted display (HMD) 552. The HMD 552 includes a front body 556 and a frame 554 (e.g., a strap or band) shaped to fit around a user's head. In some embodiments, the HMD 552 includes output audio transducers 558-1 and 558-2, as shown in FIG. 5B (e.g., transducers). In some embodiments, the front body 556 and/or the frame 554 includes one or more electronic elements, including one or more electronic displays, one or more IMUs, one or more tracking emitters or detectors, and/or any other suitable device or sensor for creating an artificial-reality experience.

Artificial-reality systems may include a variety of types of visual feedback mechanisms. For example, display devices in the AR system 500 and/or the VR system 550 may include one or more liquid-crystal displays (LCDs), light emitting diode (LED) displays, organic LED (OLED) displays, and/or any other suitable type of display screen. Artificial-reality systems may include a single display screen for both eyes or may provide a display screen for each eye, which may allow for additional flexibility for varifocal adjustments or for correcting a refractive error associated with the user's vision. Some artificial-reality systems also include optical subsystems having one or more lenses (e.g., conventional concave or convex lenses, Fresnel lenses, or adjustable liquid lenses) through which a user may view a display screen.

In addition to or instead of using display screens, some artificial-reality systems include one or more projection systems. For example, display devices in the AR system 500 and/or the VR system 550 may include micro-LED projectors that project light (e.g., using a waveguide) into display devices, such as clear combiner lenses that allow ambient light to pass through. The display devices may refract the projected light toward a user's pupil and may enable a user to simultaneously view both artificial-reality content and the real world. Artificial-reality systems may also be configured with any other suitable type or form of image projection system.

Artificial-reality systems may also include various types of computer vision components and subsystems. For example, the AR system 500 and/or the VR system 550 can include one or more optical sensors such as two-dimensional (2D) or three-dimensional (3D) cameras, time-of-flight depth sensors, single-beam or sweeping laser rangefinders, 3D LiDAR sensors, and/or any other suitable type or form of optical sensor. An artificial-reality system may process data from one or more of these sensors to identify a location of a user, to map the real world, to provide a user with context about real-world surroundings, and/or to perform a variety of other functions. For example, FIG. 5B shows VR system 550 having cameras 560-1 and 560-2 that can be used to provide depth information for creating a voxel field and a two-dimensional mesh to provide object information to the user to avoid collisions. FIG. 5B also shows that the VR system includes one or more additional cameras 562 that are configured to augment the cameras 560-1 and 560-2 by providing more information. For example, the additional cameras 562 can be used to supply color information that is not discerned by cameras 560-1 and 560-2. In some embodiments, cameras 560-1 and 560-2 and additional cameras 562 can include an optional IR cut filter configured to remove IR light from being received at the respective camera sensors.

In some embodiments, the AR system 500 and/or the VR system 550 can include haptic (tactile) feedback systems, which may be incorporated into headwear, gloves, body suits, handheld controllers, environmental devices (e.g., chairs or floormats), and/or any other type of device or system, such as the wearable devices discussed herein. The haptic feedback systems may provide various types of cutaneous feedback, including vibration, force, traction, shear, texture, and/or temperature. The haptic feedback systems may also provide various types of kinesthetic feedback, such as motion and compliance. The haptic feedback may be implemented using motors, piezoelectric actuators, fluidic systems, and/or a variety of other types of feedback mechanisms. The haptic feedback systems may be implemented independently of other artificial-reality devices, within other artificial-reality devices, and/or in conjunction with other artificial-reality devices.

The techniques described above can be used with any device for interacting with an artificial-reality environment, including the head-wearable devices of FIG. 5A-5B, but could also be used with other types of wearable devices for sensing neuromuscular signals (such as body-wearable or head-wearable devices that might have neuromuscular sensors closer to the brain or spinal column). Having thus described example wrist-wearable device and head-wearable devices, attention will now be turned to example feedback systems that can be integrated into the devices described above or be a separate device.

Example Systems

Figure 6A:
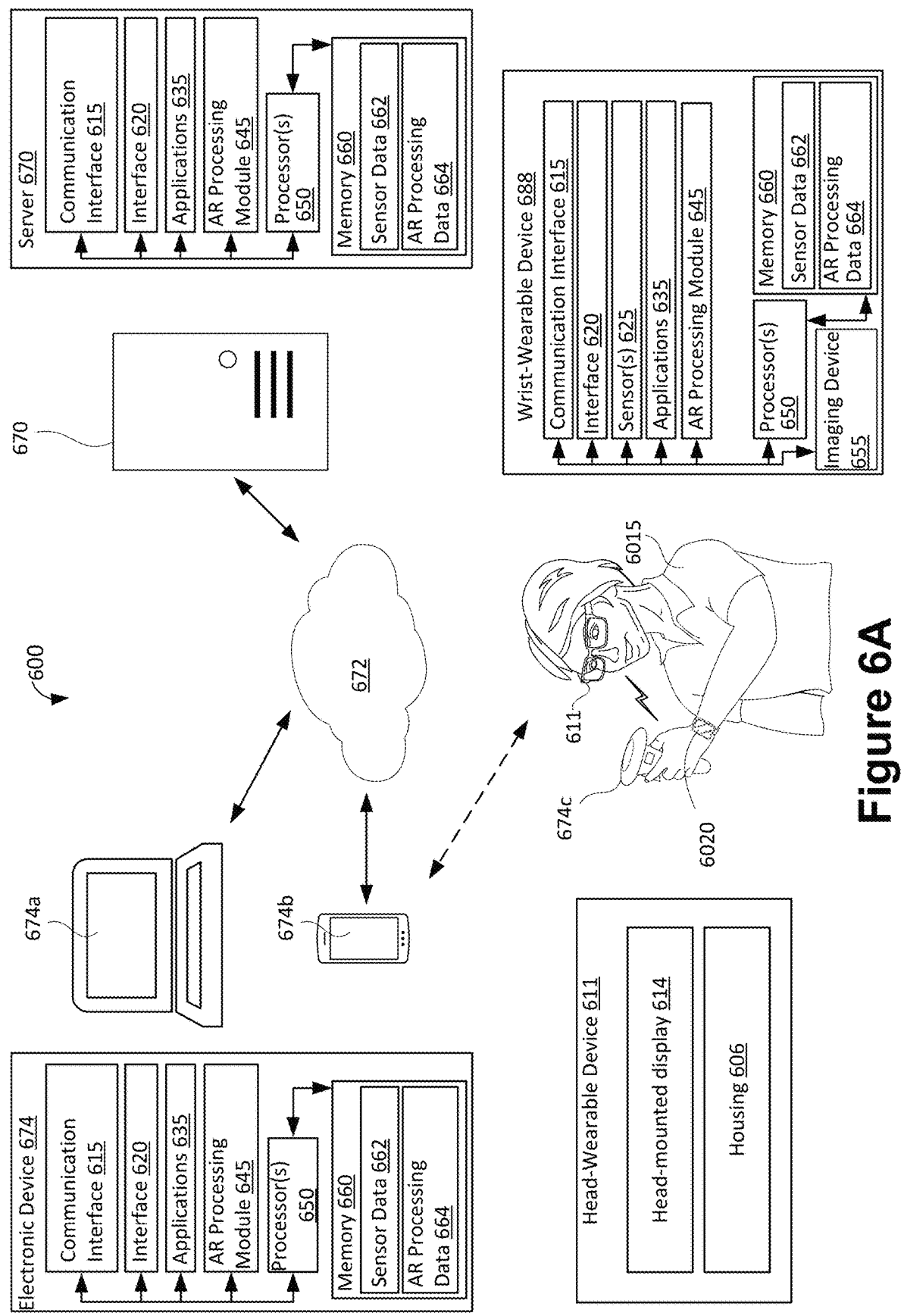
FIGS. 6A and 6B are block diagrams illustrating an example artificial-reality system in accordance with some embodiments.
Figure 6B:
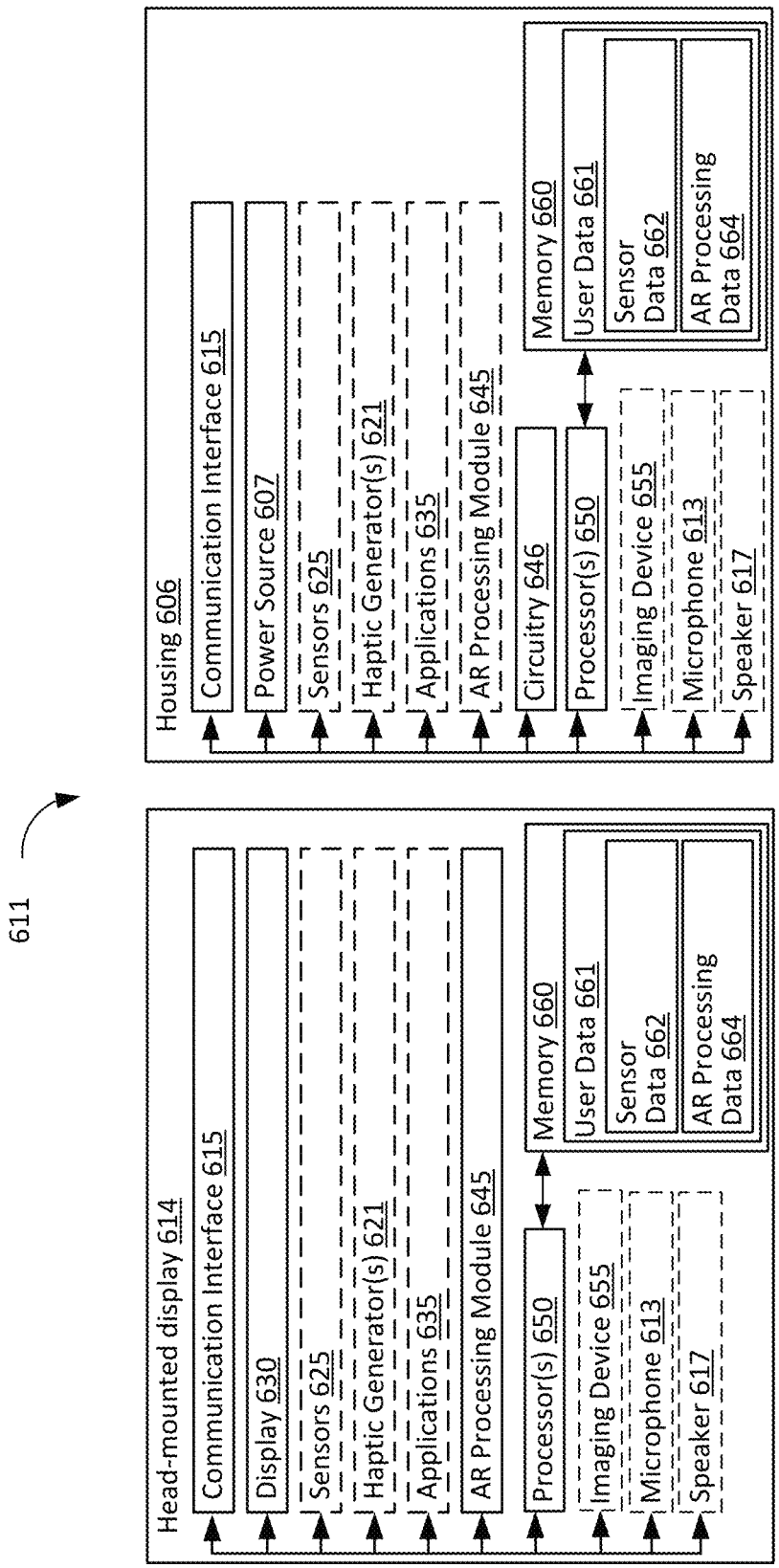

FIGS. 6A and 6B are block diagrams illustrating an example artificial-reality system in accordance with some embodiments. The system 600 includes one or more devices for facilitating an interactivity with an artificial-reality environment in accordance with some embodiments. For example, the head-wearable device 611 can present to the user 6015 with a user interface within the artificial-reality environment. As a non-limiting example, the system 600 includes one or more wearable devices, which can be used in conjunction with one or more computing devices. In some embodiments, the system 600 provides the functionality of a virtual-reality device, an augmented-reality device, a mixed-reality device, hybrid-reality device, or a combination thereof. In some embodiments, the system 600 provides the functionality of a user interface and/or one or more user applications (e.g., games, word processors, messaging applications, calendars, clocks, etc.).

The system 600 can include one or more of servers 670, electronic devices 674 (e.g., a computer, 674a, a smartphone 674b, a controller 674c, and/or other devices), head-wearable devices 611 (e.g., the AR system 500 or the VR system 550), and/or wrist-wearable devices 688 (e.g., the wrist-wearable device 6020). In some embodiments, the one or more of servers 670, electronic devices 674, head-wearable devices 611, and/or wrist-wearable devices 688 are communicatively coupled via a network 672. In some embodiments, the head-wearable device 611 is configured to cause one or more operations to be performed by a communicatively coupled wrist-wearable device 688, and/or the two devices can also both be connected to an intermediary device, such as a smartphone 674b, a controller 674c, or other device that provides instructions and data to and between the two devices. In some embodiments, the head-wearable device 611 is configured to cause one or more operations to be performed by multiple devices in conjunction with the wrist-wearable device 688. In some embodiments, instructions to cause the performance of one or more operations are controlled via an artificial-reality processing module 645. The artificial-reality processing module 645 can be implemented in one or more devices, such as the one or more of servers 670, electronic devices 674, head-wearable devices 611, and/or wrist-wearable devices 688. In some embodiments, the one or more devices perform operations of the artificial-reality processing module 645, using one or more respective processors, individually or in conjunction with at least one other device as described herein. In some embodiments, the system 600 includes other wearable devices not shown in FIG. 6A and FIG. 6B, such as rings, collars, anklets, gloves, and the like.

In some embodiments, the system 600 provides the functionality to control or provide commands to the one or more computing devices 674 based on a wearable device (e.g., head-wearable device 611 or wrist-wearable device 688) determining motor actions or intended motor actions of the user. A motor action is an intended motor action when before the user performs the motor action or before the user completes the motor action, the detected neuromuscular signals travelling through the neuromuscular pathways can be determined to be the motor action. Motor actions can be detected based on the detected neuromuscular signals, but can additionally (using a fusion of the various sensor inputs), or alternatively, be detected using other types of sensors (such as cameras focused on viewing hand movements and/or using data from an inertial measurement unit that can detect characteristic vibration sequences or other data types to correspond to particular in-air hand gestures). The one or more computing devices include one or more of a head-mounted display, smartphones, tablets, smart watches, laptops, computer systems, augmented reality systems, robots, vehicles, virtual avatars, user interfaces, a wrist-wearable device, and/or other electronic devices and/or control interfaces.

In some embodiments, the motor actions include digit movements, hand movements, wrist movements, arm movements, pinch gestures, index finger movements, middle finger movements, ring finger movements, little finger movements, thumb movements, hand clenches (or fists), waving motions, and/or other movements of the user's hand or arm.

In some embodiments, the user can define one or more gestures using the learning module. In some embodiments, the user can enter a training phase in which a user defined gesture is associated with one or more input commands that when provided to a computing device cause the computing device to perform an action. Similarly, the one or more input commands associated with the user-defined gesture can be used to cause a wearable device to perform one or more actions locally. The user-defined gesture, once trained, is stored in the memory 660. Similar to the motor actions, the one or more processors 650 can use the detected neuromuscular signals by the one or more sensors 625 to determine that a user-defined gesture was performed by the user.

The electronic devices 674 can also include a communication interface 615, an interface 620 (e.g., including one or more displays, lights, speakers, and haptic generators), one or more sensors 625, one or more applications 635, an artificial-reality processing module 645, one or more processors 650, and memory 660. The electronic devices 674 are configured to communicatively couple with the wrist-wearable device 688 and/or head-wearable device 611 (or other devices) using the communication interface 615. In some embodiments, the electronic devices 674 are configured to communicatively couple with the wrist-wearable device 688 and/or head-wearable device 611 (or other devices) via an application programming interface (API). In some embodiments, the electronic devices 674 operate in conjunction with the wrist-wearable device 688 and/or the head-wearable device 611 to determine a hand gesture and cause the performance of an operation or action at a communicatively coupled device.

The server 670 includes a communication interface 615, one or more applications 635, an artificial-reality processing module 645, one or more processors 650, and memory 660. In some embodiments, the server 670 is configured to receive sensor data from one or more devices, such as the head-wearable device 611, the wrist-wearable device 688, and/or electronic device 674, and use the received sensor data to identify a gesture or user input. The server 670 can generate instructions that cause the performance of operations and actions associated with a determined gesture or user input at communicatively coupled devices, such as the head-wearable device 611.

The head-wearable device 611 includes smart glasses (e.g., the augmented-reality glasses), artificial reality headsets (e.g., VR/AR headsets), or other head worn device. In some embodiments, one or more components of the head-wearable device 611 are housed within a body of the HMD 614 (e.g., frames of smart glasses, a body of a AR headset, etc.). In some embodiments, one or more components of the head-wearable device 611 are stored within or coupled with lenses of the HMD 614. Alternatively or in addition, in some embodiments, one or more components of the head-wearable device 611 are housed within a modular housing 606. The head-wearable device 611 is configured to communicatively couple with other electronic device 674 and/or a server 670 using communication interface 615 as discussed above.

FIG. 6B describes additional details of the HMD 614 and modular housing 606 described above in reference to 6A, in accordance with some embodiments.

The housing 606 include(s) a communication interface 615, circuitry 646, a power source 607 (e.g., a battery for powering one or more electronic components of the housing 606 and/or providing usable power to the HMD 614), one or more processors 650, and memory 660. In some embodiments, the housing 606 can include one or more supplemental components that add to the functionality of the HMD 614. For example, in some embodiments, the housing 606 can include one or more sensors 625, an AR processing module 645, one or more haptic generators 621, one or more imaging devices 655, one or more microphones 613, one or more speakers 617, etc. The housing 106 is configured to couple with the HMD 614 via the one or more retractable side straps. More specifically, the housing 606 is a modular portion of the head-wearable device 611 that can be removed from head-wearable device 611 and replaced with another housing (which includes more or less functionality). The modularity of the housing 606 allows a user to adjust the functionality of the head-wearable device 611 based on their needs.

In some embodiments, the communications interface 615 is configured to communicatively couple the housing 606 with the HMD 614, the server 670, and/or other electronic device 674 (e.g., the controller 674c, a tablet, a computer, etc.). The communication interface 615 is used to establish wired or wireless connections between the housing 606 and the other devices. In some embodiments, the communication interface 615 includes hardware capable of data communications using any of a variety of custom or standard wireless protocols (e.g., IEEE 802.15.4, Wi-Fi, ZigBee, 6LoWPAN, Thread, Z-Wave, Bluetooth Smart, ISA100.11a, WirelessHART, or MiWi), custom or standard wired protocols (e.g., Ethernet or HomePlug), and/or any other suitable communication protocol. In some embodiments, the housing 606 is configured to communicatively couple with the HMD 614 and/or other electronic device 674 via an application programming interface (API).

In some embodiments, the power source 607 is a battery. The power source 607 can be a primary or secondary battery source for the HMD 614. In some embodiments, the power source 607 provides useable power to the one or more electrical components of the housing 606 or the HMD 614. For example, the power source 607 can provide usable power to the sensors 621, the speakers 617, the HMD 614, and the microphone 613. In some embodiments, the power source 607 is a rechargeable battery. In some embodiments, the power source 607 is a modular battery that can be removed and replaced with a fully charged battery while it is charged separately.

The one or more sensors 625 can include heart rate sensors, neuromuscular-signal sensors (e.g., electromyography (EMG) sensors), SpO2 sensors, altimeters, thermal sensors or thermal couples, ambient light sensors, ambient noise sensors, and/or inertial measurement units (IMU)s. Additional non-limiting examples of the one or more sensors 625 include, e.g., infrared, pyroelectric, ultrasonic, microphone, laser, optical, Doppler, gyro, accelerometer, resonant LC sensors, capacitive sensors, acoustic sensors, and/or inductive sensors. In some embodiments, the one or more sensors 625 are configured to gather additional data about the user (e.g., an impedance of the user's body). Examples of sensor data output by these sensors includes body temperature data, infrared range-finder data, positional information, motion data, activity recognition data, silhouette detection and recognition data, gesture data, heart rate data, and other wearable device data (e.g., biometric readings and output, accelerometer data). The one or more sensors 625 can include location sensing devices (e.g., GPS) configured to provide location information. In some embodiment, the data measured or sensed by the one or more sensors 625 is stored in memory 660. In some embodiments, the housing 606 receives sensor data from communicatively coupled devices, such as the HMD 614, the server 670, and/or other electronic device 674. Alternatively, the housing 606 can provide sensors data to the HMD 614, the server 670, and/or other electronic device 674.

The one or more haptic generators 621 can include one or more actuators (e.g., eccentric rotating mass (ERM), linear resonant actuators (LRA), voice coil motor (VCM), piezo haptic actuator, thermoelectric devices, solenoid actuators, ultrasonic transducers or sensors, etc.). In some embodiments, the one or more haptic generators 621 are hydraulic, pneumatic, electric, and/or mechanical actuators. In some embodiments, the one or more haptic generators 621 are part of a surface of the housing 606 that can be used to generate a haptic response (e.g., a thermal change at the surface, a tightening or loosening of a band, increase or decrease in pressure, etc.). For example, the one or more haptic generators 625 can apply vibration stimulations, pressure stimulations, squeeze simulations, shear stimulations, temperature changes, or some combination thereof to the user. In addition, in some embodiments, the one or more haptic generators 621 include audio generating devices (e.g., speakers 617 and other sound transducers) and illuminating devices (e.g., light-emitting diodes (LED) s, screen displays, etc.). The one or more haptic generators 621 can be used to generate different audible sounds and/or visible lights that are provided to the user as haptic responses. The above list of haptic generators is non-exhaustive; any affective devices can be used to generate one or more haptic responses that are delivered to a user.

In some embodiments, the one or more applications 635 include social-media applications, banking applications, health applications, messaging applications, web browsers, gaming application, streaming applications, media applications, imaging applications, productivity applications, social applications, etc. In some embodiments, the one or more applications 635 include artificial reality applications. The one or more applications 635 are configured to provide data to the head-wearable device 611 for performing one or more operations. In some embodiments, the one or more applications 635 can be displayed via a display 630 of the head-wearable device 611 (e.g., via the HMD 614).

In some embodiments, instructions to cause the performance of one or more operations are controlled via an artificial reality (AR) processing module 645. The AR processing module 645 can be implemented in one or more devices, such as the one or more of servers 670, electronic devices 674, head-wearable devices 611, and/or wrist-wearable devices 670. In some embodiments, the one or more devices perform operations of the AR processing module 645, using one or more respective processors, individually or in conjunction with at least one other device as described herein. In some embodiments, the AR processing module 645 is configured process signals based at least on sensor data. In some embodiments, the AR processing module 645 is configured process signals based on image data received that captures at least a portion of the user hand, mouth, facial expression, surrounding, etc. For example, the housing 606 can receive EMG data and/or IMU data from one or more sensors 625 and provide the sensor data to the AR processing module 645 for a particular operation (e.g., gesture recognition, facial recognition, etc.). The AR processing module 645, causes a device communicatively coupled to the housing 606 to perform an operation (or action). In some embodiments, the AR processing module 645 performs different operations based on the sensor data and/or performs one or more actions based on the sensor data.

In some embodiments, the one or more imaging devices 655 can include an ultra-wide camera, a wide camera, a telephoto camera, a depth-sensing cameras, or other types of cameras. In some embodiments, the one or more imaging devices 655 are used to capture image data and/or video data. The imaging devices 655 can be coupled to a portion of the housing 606. The captured image data can be processed and stored in memory and then presented to a user for viewing. The one or more imaging devices 655 can include one or more modes for capturing image data or video data. For example, these modes can include a high-dynamic range (HDR) image capture mode, a low light image capture mode, burst image capture mode, and other modes. In some embodiments, a particular mode is automatically selected based on the environment (e.g., lighting, movement of the device, etc.). For example, a wrist-wearable device with HDR image capture mode and a low light image capture mode active can automatically select the appropriate mode based on the environment (e.g., dark lighting may result in the use of low light image capture mode instead of HDR image capture mode). In some embodiments, the user can select the mode. The image data and/or video data captured by the one or more imaging devices 655 is stored in memory 660 (which can include volatile and non-volatile memory such that the image data and/or video data can be temporarily or permanently stored, as needed depending on the circumstances).

The circuitry 646 is configured to facilitate the interaction between the housing 606 and the HMD 614. In some embodiments, the circuitry 646 is configured to regulate the distribution of power between the power source 607 and the HMD 614. In some embodiments, the circuitry 746 is configured to transfer audio and/or video data between the HMD 614 and/or one or more components of the housing 606.

The one or more processors 650 can be implemented as any kind of computing device, such as an integrated system-on-a-chip, a microcontroller, a fixed programmable gate array (FPGA), a microprocessor, and/or other application specific integrated circuits (ASICs). The processor may operate in conjunction with memory 660. The memory 660 may be or include random access memory (RAM), read-only memory (ROM), dynamic random access memory (DRAM), static random access memory (SRAM) and magnetoresistive random access memory (MRAM), and may include firmware, such as static data or fixed instructions, basic input/output system (BIOS), system functions, configuration data, and other routines used during the operation of the housing and the processor 650. The memory 660 also provides a storage area for data and instructions associated with applications and data handled by the processor 650.

In some embodiments, the memory 660 stores at least user data 661 including sensor data 662 and AR processing data 664. The sensor data 662 includes sensor data monitored by one or more sensors 625 of the housing 606 and/or sensor data received from one or more devices communicative coupled with the housing 606, such as the HMD 614, the smartphone 674*b*, the controller 674*c*, etc. The sensor data 662 can include sensor data collected over a predetermined period of time that can be used by the AR processing module 645. The AR processing data 664 can include one or more one or more predefined camera-control gestures, user defined camera-control gestures, predefined non-camera-control gestures, and/or user defined non-camera-control gestures. In some embodiments, the AR processing data 664 further includes one or more predetermined threshold for different gestures.

The HMD 614 includes a communication interface 615, a display 630, an AR processing module 645, one or more processors, and memory. In some embodiments, the HMD 614 includes one or more sensors 625, one or more haptic generators 621, one or more imaging devices 655 (e.g., a camera), microphones 613, speakers 617, and/or one or more applications 635. The HMD 614 operates in conjunction with the housing 606 to perform one or more operations of a head-wearable device 611, such as capturing camera data, presenting a representation of the image data at a coupled display, operating one or more applications 635, and/or allowing a user to participate in an AR environment.

Any data collection performed by the devices described herein and/or any devices configured to perform or cause the performance of the different embodiments described above in reference to any of the Figures, hereinafter the "devices," is done with user consent and in a manner that is consistent with all applicable privacy laws. Users are given options to allow the devices to collect data, as well as the option to limit or deny collection of data by the devices. A user is able to opt-in or opt-out of any data collection at any time. Further, users are given the option to request the removal of any collected data.

It will be understood that, although the terms "first," "second," etc. may be used herein to describe various elements, these elements should not be limited by these terms. These terms are only used to distinguish one element from another.

The terminology used herein is for the purpose of describing particular embodiments only and is not intended to be limiting of the claims. As used in the description of the embodiments and the appended claims, the singular forms "a," "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" can be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" can be construed to mean "upon determining" or "in response to determining" or "in accordance with a determination" or "upon detecting" or "in response to detecting" that the stated condition precedent is true, depending on the context.

The foregoing description, for purpose of explanation, has been described with reference to specific embodiments. However, the illustrative discussions above are not intended to be exhaustive or to limit the claims to the precise forms disclosed. Many modifications and variations are possible in view of the above teachings. The embodiments were chosen and described in order to best explain principles of operation and practical applications, to thereby enable others skilled in the art.

What is claimed is:

1. A wrist-wearable device, comprising:
   a first skin-contact portion of a band of the wrist-wearable device that:
   (i) includes a first flexible printed circuit board,
   (ii) is coupled with a first set of biopotential-signal sensors for detecting first biopotential signals that are provided to the first flexible printed circuit board, and
   (iii) is coupled with an elastic material that extends beyond an end of the first skin-contact portion of the band and the elastic material is not directly coupled with the first-set of biopotential-signal sensors; and
   a second skin-contact portion of the band of the wrist-wearable device that is separated from the first skin-contact portion of the band by a capsule structure, the second skin-contact portion:
   (i) including a second flexible printed circuit board,
   (ii) coupled with a second set of biopotential-signal sensors for detecting biopotential signals that are provided to the second flexible printed circuit board, and
   (iii) coupled with a receiving loop for receiving the elastic material to affix the band to a body part of a wearer of the wrist-wearable device and the receiving loop is not directly coupled with the second set of biopotential-signal sensors,
   wherein the first skin-contact portion and the second skin-contact portion are made of a same material that is distinct from the elastic material, such that when the wrist-wearable device is worn on the wrist of a user the elastic material is configured to stretch to affix the band to a wrist of the user through the receiving loop and the first and second skin-contact portions are not configured to stretch to thereby cause at least some of the first and second sets of biopotential-signal sensors to contact skin of the user.

2. The wrist-wearable device of claim 1, wherein the elastic material is at least 25% less in width than the first skin-contact portion of the band.

3. The wrist-wearable device of claim 1, wherein the receiving loop and elastic material are configured such that stress applied to the receiving loop and elastic material are substantially not transferred to both the first flexible printed circuit board and the second flexible printed circuit board, when the wrist-wearable device is worn on a wrist of the user.

4. The wrist-wearable device of claim 1, wherein:
   the elastic material includes a loop portion of a hook and loop fastener, wherein the loop portion includes a plurality of loops,
   the first skin-contact portion of the band includes a hook portion of the hook and loop fastener and is configured to attach with the loop portion after the elastic material has been passed through the receiving loop of the second skin-contact portion to secure the wrist-wearable device to a wrist of the user, wherein the hook portion includes a plurality of hooks.

5. The wrist-wearable device of claim 4, wherein the first skin-contact portion of the band and the loop portion of the hook and loop fastener are sewn together.

6. The wrist-wearable device of claim 4, wherein the hook portion of the hook and loop fastener is a distinct and separate material from the elastic material, and the hook portion of the hook and loop fastener is adhered to a top part of the first skin-contact portion, the top part being opposite to a bottom part of the first skin-contact portion at which the first set of biopotential-signal sensors are coupled.

7. The wrist-wearable device of claim 4, wherein elastic material and the receiving loop are attached through respective cutouts of the first and second skin-contact portions, and then adhered to those portions.

8. The wrist-wearable device of claim 1, wherein a number of the first set of biopotential-signal sensors is larger than a number of the second set of biopotential-signal sensors.

9. The wrist-wearable device of claim 1, wherein the first set of biopotential-signal sensors contains fewer biopotential-signal sensors than the second set of biopotential-signal sensors.

10. The wrist-wearable device of claim 1, wherein the first and second flexible printed circuit boards are directly adhered to the first and second skin-contact portions.

11. The wrist-wearable device of claim 1, wherein the first skin-contact portion of the band and the second skin-contact portion of the band each include cutouts for the first set of biopotential-signal sensors and the second set of biopotential-signal sensors to pass-through, respectively.

12. The wrist-wearable device of claim 1, wherein contact points of the first and second flexible printed circuit boards are exposed for connection with a capsule portion, wherein the capsule portion connects to both the first and second flexible printed circuit boards.

13. The wrist-wearable device of claim 12, wherein the capsule portion connects to both the first and second flexible printed circuit boards via multiple fasteners and an adhesive.

14. The wrist-wearable device of claim 1, wherein the elastic material is partially adhered to a top part of the first skin-contact portion.

15. The wrist-wearable device of claim 1, wherein the elastic material is 3.5-5.5 inches in length.

16. The wrist-wearable device of claim 1, wherein an end of the elastic material includes a portion that is folded over on itself and the folded over potion is between 4/16 and 6/16 of an inch.

17. The wrist-wearable device of claim 1, wherein the elastic material includes a hook and loop portion that is 2.5-4.5 inches in length.

18. A method of manufacturing a wrist-wearable device, comprising:
   providing a first skin-contact portion of a band of the wrist-wearable device that is produced by:
      (i) coupling a first set of biopotential-signal sensors for detecting first biopotential signals with a first flexible printed circuit board to produce a first biopotential sensor sub-assembly;
      (ii) coupling the first biopotential sensor sub-assembly with the first skin-contact portion of the band; and
      (iii) coupling an elastic material to the first skin-contact portion of the band that extends beyond an end of the first skin-contact portion of the band and the elastic material is not directly coupled with the first set of biopotential-signal sensors; and
   providing a second skin-contact portion of the band of the wrist-wearable device that is coupled to the first skin-contact portion of the band by a capsule structure, the second skin-contact portion is produced by:
      (i) coupling a second set of biopotential-signal sensors for detecting biopotential signals that are provided to a second flexible printed circuit board to produce a second biopotential sensor sub-assembly;
      (ii) coupling the second biopotential sensor sub-assembly with the second skin-contact portion of the band; and
      (iii) coupling a receiving loop for receiving the elastic material to affix the band to a body part of a wearer of the wrist-wearable device and the receiving loop is not directly coupled with the second set of biopotential sensors,
   wherein the first skin-contact portion and the second skin-contact portion are made of a same material that is distinct from the elastic material, such that when the wrist-wearable device is worn on the wrist of a user the elastic material is configured to stretch to affix the band to the wrist of the user through the receiving loop and the first and second skin-contact portions are not configured to stretch to thereby cause at least some of the first and second sets of biopotential-signal sensors to contact skin of the user.

19. The method of manufacturing the wrist-wearable device of claim 18, wherein the first skin-contact portion of the band and the second skin-contact portion are part of a continuous textile that was configured to be placed in a jig-alignment assembly, the method of manufacturing further includes:
   trimming the first skin-contact portion of the band and the second skin-contact portion to produce a first trimmed-skin-contact portion of the band and a second trimmed-skin-contact portion, wherein the first trimmed-skin-contact portion of the band and the second trimmed-skin-contact portion are configured to be separately coupled to the capsule structure.

20. A system that includes:
   an artificial-reality headset; and
   one or more wrist wearable devices, wherein at least one of the one or more wrist wearable devices comprises:
      a first skin-contact portion of a band of the wrist-wearable device that:
         (i) includes a first flexible printed circuit board,
         (ii) is coupled with a first set of biopotential-signal sensors for detecting first biopotential signals that are provided to the first flexible printed circuit board, and
         (iii) is coupled with an elastic material that extends beyond an end of the first skin-contact portion of the band and the elastic material is not directly coupled with the first set of biopotential-signal sensors; and
      a second skin-contact portion of the band of the wrist-wearable device that is separated from the first skin-contact portion of the band by a capsule structure, the second skin-contact portion:
         (i) including a second flexible printed circuit board,
         (ii) coupled with a second set of biopotential-signal sensors for detecting biopotential signals that are provided to the second flexible printed circuit board, and
         (iii) coupled with a receiving loop for receiving the elastic material to affix the band to a body part of a wearer of the wrist-wearable device and the receiving loop is not directly coupled with the second set of biopotential sensors,
   wherein the first skin-contact portion and the second skin-contact portion are made of a same material that is distinct from the elastic material, such that when the wrist-wearable device is worn on the wrist of a user the elastic material is configured to stretch to affix the band to a wrist of the user through the receiving loop and the first and second skin-contact portions are not configured to stretch to thereby cause at least some of the first and second sets of biopotential-signal sensors to contact skin of the user.

* * * * *